US008173636B2

(12) United States Patent
Bradbury et al.

(10) Patent No.: US 8,173,636 B2
(45) Date of Patent: May 8, 2012

(54) HYDROXYLTHIENOQUINOLONES AND RELATED COMPOUNDS AS ANTI-INFECTIVE AGENTS

(75) Inventors: Barton James Bradbury, Wallingford, CT (US); Milind Deshpande, Madison, CT (US); Akihiro Hashimoto, Branford, CT (US); Ha Young Kim, Cheshire, CT (US); Edlaine Lucien, New Haven, CT (US); Godwin Pais, Hamden, CT (US); Michael Pucci, Kensington, CT (US); Qiuping Wang, Bethany, CT (US); Jason Allan Wiles, Hamden, CT (US); Avinash Phadke, Branfod, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 218 days.

(21) Appl. No.: 12/754,057

(22) Filed: Apr. 5, 2010

(65) Prior Publication Data

US 2010/0256112 A1    Oct. 7, 2010

Related U.S. Application Data

(60) Provisional application No. 61/166,371, filed on Apr. 3, 2009.

(51) Int. Cl.
*C07D 495/04*    (2006.01)
*A61K 31/4743*    (2006.01)
*A61K 31/496*    (2006.01)

(52) U.S. Cl. ............... 514/210.21; 514/291; 514/253.03; 546/80; 544/361

(58) Field of Classification Search ............ 514/210.21, 514/291, 253.03; 546/80; 544/361
See application file for complete search history.

(56) References Cited

U.S. PATENT DOCUMENTS

| 4,767,762 | A | 8/1988 | Chu |
|---|---|---|---|
| 5,071,848 | A | 12/1991 | Chu et al. |
| 5,087,621 | A | 2/1992 | Pinol et al. |
| 5,387,748 | A | 2/1995 | Demuth, Jr. et al. |
| 5,519,016 | A | 5/1996 | Kimura et al. |
| 5,631,256 | A | 5/1997 | Demuth, Jr. et al. |
| 5,646,163 | A | 7/1997 | Demuth, Jr. et al. |
| 5,688,791 | A | 11/1997 | Kimura et al. |
| 2005/0075363 | A1 | 4/2005 | Bradbury et al. |
| 2006/0235041 | A1 | 10/2006 | Bradbury et al. |
| 2007/0049586 | A1 | 3/2007 | Bradbury et al. |

FOREIGN PATENT DOCUMENTS

| EP | 0878194 A1 | 11/1998 |
|---|---|---|
| JP | 01160985 | 6/1989 |
| JP | 01193275 | 8/1989 |
| JP | 01265092 | 10/1989 |
| JP | 02174784 | 7/1990 |
| JP | 02243692 | 9/1990 |
| JP | 02255687 | 10/1990 |
| JP | 0358992 | 3/1991 |
| JP | 03209367 | 9/1991 |
| JP | 03223289 | 10/1991 |
| JP | 03223289 A | * 10/1991 |
| JP | 09288105 | 4/1997 |
| JP | 10130149 | 5/1998 |
| WO | 9529894 A1 | 11/1995 |
| WO | 0248138 A1 | 6/2002 |

OTHER PUBLICATIONS

Chu, et al., "Practical Synthesis of Iminochlorothioformates: Application of Iminochlorothioformates in the Synthesis of Novel 2,3,4,9-Tetrahydroisothiazolo[5,4-b][1,8]naphthyridine-3,4-diones and 2,3,4,9-Tetrahydroisothiazolo[5,4-b] quinoline-3,4-dione Derivatives," J. Heterocyclic Chem. 27: 1191-1195 (1990).

Chu, et al., "Structure-Activity Relationships in Quinolone Antibacterials: Design, Synthesis and Biological Activities of Novel Isothiazoloquinolones," Drugs Exptl. Clin. Res. 14(6): 379-383 (1988).

Chung, et al., "Geometry Mapping of N(1)-Substituents of Quinolone Antibacterials and the Antibacterial Mode of Actions," Koren J. of Med. Chem. 3(2): 148-161 (1993).

Chu, et al., "Syntheses of 6-Fluoro-7-piperazin-1-yl-9-cyclopropyl-2,3,4,9-tetrahydroisothiazolo[5,4-b]quinoline-3,4-dione and 6-Fluoro-7-piperazin-1-yl-9-p-fluorophenyl-2,3,4,9-tetrahydroisothiazolo[5,4-b]quinoline-3,4-dione [1]," J. Heterocyclic Chem. 27: 839-843 (1990).

Frigola, et al., "7-Azetidinylquinolones as Antibacterial Agents. Synthesis and Structure-Activity Relationships," J. Med. Chem. 36: 801-810 (1993).

(Continued)

*Primary Examiner* — Kahsay T Habte
(74) *Attorney, Agent, or Firm* — Cantor Colburn LLP

(57) ABSTRACT

Disclosed herein are hydroxylthienoquinolones and related compounds and their pharmaceutically acceptable salts useful as antiviral agents and having the general formula

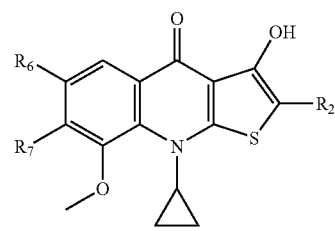

in which the variables $R_2$, $R_6$, and $R_7$ are defined herein. Certain compounds provided herein possess potent antibacterial, antiprotozoal, or antifungal activity and are particularly efficacious for the treatment of MRSA infections. The invention also provides pharmaceutical compositions, pharmaceutical compositions containing a hydroxylthienoquinolone in combination with one or more other active agent, and methods of treating microbial infections in animals by administering an effective amount of a hydroxylthienoquinolone or related compound to an animal suffering from a microbial infection.

21 Claims, No Drawings

OTHER PUBLICATIONS

Frigola, et al., "7-Azetidinylquinolones as Antibacterial Agents. 2. Synthesis and Biological Activity of 7-(2,3-Disubstituted-1-azetidinyl)-4-oxoquinoline- and -1,8-naphthyridine-3-carboxylic Acids. Properties adn Structure—Activity Relationships of Quinolones with an Azetidine Moiety," J. Med. Chem. 37: 4195-4210 (1994).

Inagaki, et al., "Synthesis and Structure—Activity Relationships of 5-Amino-6-fluoro-1[1R,2S)-2-fluorocyclopropan-1-yl]-8-methylquinolonecarboxylic Acid Antibacterials Having Fluorinated 7-[(3R)-3-(1-Aminocyclopropan-1-yl) pyrrolidin-1-yl] Substituents1," J. Med. Chem. 46: 1005-1015 (2003).

Ishiyama, et al., "Palladium(0)-Catalyzed Cross-Coupling Reaction of Alkoxydiboron with Haloarenes: A Direct Procedure for Arylboronic Esters," J. Org. Chem. 60: 7508-7510 (1995).

Kiely, et al., "Synthesis of 7-(Alkenyl, Cycloalkenyl, and 1,2,3,6-Tetrahydro-4-pyridinyl)quinolones," J. Heterocyclic Chem. 28: 1581-1585 (1991).

Kohlbrenner, et al., "Induction of Calf Thymus Topoisomerase II-Mediated DNA Breakage by the Antibacterial Isothiazoloquinolones A-65281 and A-65282," Antimicrobial Agents and Chemotherapy 36(1): 81-86 (1992).

Laborde, et al., "Novel 7-Substituted Quinolone Antibacterial Agents. Synthesis of 7-Alkenyl, Cycloalkenyl, and 1,2,3,6-Tetrahydro-4-pyridinyl-1,8-naphthyridines [1]," J. Heterocyclic Chem. 28: 191-198 (1991).

Laborde, et al., "Quinolone Antibacterials: Synthesis and Biological Activity of Carbon Isosteres of the 1-Piperazinyl and 3-Amino-1-pyrrolidinyl Side Chains," J. Med. Chem. 36: 1964-1970 (1993).

Lenoir, et al., "An Efficient Method for the Synthesis of (R)-3-(1-Amino-1-methylethyl)pyrrolidines for the Antiinfective Agent, PD 138312," Tetrahedron: Asymmetry 5(7): 1131-1134 (1994).

Nahm, et al., "Quinolone Compounds with Carboxylic Equivalents and Semiempiracal Calculations on their Tautomers," Bioorganic & Medicinal Chemistry Letters 3(13): 2631-2634 (1993).

Potemkin, et al., "Theoretical Investigation of the Antituberculous Activity of Membranotropic Podands," Pharmaceutical Chemistry Journal 37(9): 468-472 (2003).

Reuman, et al., "Synthesis and Antibacterial Activity of Some Novel 1-Substituted 1,4-Dihydro-4-oxo-7pyridinyl-3-quinolinecarboxylic Acids. Potent Antistaphylococcal Agents," J. Med. Chem. 38(14): 2531-2540 (1995).

Shen, et al., "Mechanism of Inhibition of DNA Gyrase by Quinolone Antibacterials: A Cooperative Drug-DNA Binding Model," Biochemistry 28: 3886-3894 (1989).

Tamao, et al., "Introduction to Cross-Coupling Reactions," Topics in Current Chemistry 219: 1-9 (2002).

Wierenga, et al., "General, Efficient, One-Step Synthesis of b-Keto Esters," American Chemical Society 44: 310-311 (1979).

Bhagwat, et al., "The Anti-Methicillin-Resistant *Staphylococcus aureus* Quinolone WCK 771 Has Potent Activity against Sequentially Selected Mutants, Has a Narrow Mutant Selection Window against Quinolone-Resistant *Staphylococcus aureus*, and Preferentially Targets DNA Gyrase," Antimicrobial Agents and Chemotherapy, 50(11): 3568-3579 (2006).

Ikee, et al., "Synthesis and Antibacterial activities of new quinolone derivatives utilizing 1-azabicyclo[1.1.0]butane," Bioorganic & Medicinal Chemistry Letters, 17: 942-945 (2007).

International Search Report for International Application No. PCT/US2010/029938 dated Jan. 26, 2011.

Lee, et al., "Syntheses and Antibacterial Activities of New Quinolones Containing cis- or trans-3-Amino-4-methylthiomethylpyrrolidine Moiety," Korean Journal of Life Science, 13(6): 943-949 (2003).

Pucci, et al., "In Vitro and in Vivo Antibacterial Activities of Heteroaryl Isothiazolones against Resistant Gram-Positive Pathogens," Antimicrobial Agents and Chemotherapy, 51(4): 1259-1267 (2007).

Sakagami, et al., "Anti-VRE and Anti-MRSA Activities of New Quinolones and Their Synergism with Commercial Antibiotics. Part 2," Biocontrol Science, 13(3): 103-109 (2008).

Written Opinion for International Application No. PCT/US2010/029938 dated Jan. 26, 2011.

* cited by examiner

HYDROXYLTHIENOQUINOLONES AND RELATED COMPOUNDS AS ANTI-INFECTIVE AGENTS

CROSS REFERENCE TO RELATED APPLICATION

This application claims priority from U.S. provisional application No. 61/166,371, filed 3 Apr. 2009, which is hereby incorporated by reference in its entirety.

FIELD OF THE INVENTION

Disclosed herein are hydroxylthienoquinolones and related compounds useful as antimicrobial agents. Certain compounds provided herein possess potent antibacterial, antiprotozoal, or antifungal activity. Particular compounds provided herein are also potent and/or selective inhibitors of prokaryotic DNA synthesis and prokaryotic reproduction. The invention also provides anti-microbial compositions, including pharmaceutical compositions, containing one or more carrier, diluents, and/or excipients. The invention provides pharmaceutical compositions containing a hydroxylthienoquinolone or related compound as the only active agent or containing a hydroxylthienoquinolone or related compound in combination with one or more other active agent, such as one or more other antimicrobial or antifungal agent. The invention further provides methods for treating microbial infections in animals by administering an effective amount of a hydroxylthienoquinolone or related compound to an animal suffering from a microbial infection. The invention also provides methods of inhibiting microbial growth and survival by applying an effective amount of a hydroxylthienoquinolones or related compound.

BACKGROUND OF THE INVENTION

Antimicrobial compounds are compounds capable of destroying or suppressing the growth or reproduction of microorganisms, such as bacteria, protozoa, mycoplasma, yeast, and fungi. The mechanisms by which antimicrobial compounds act vary. However, they are generally believed to function in one or more of the following ways: by inhibiting cell wall synthesis or repair; by altering cell wall permeability; by inhibiting protein synthesis; or by inhibiting synthesis of nucleic acids. For example, beta-lactam antibacterials inhibit the essential penicillin binding proteins (PBPs) in bacteria, which are responsible for cell wall synthesis. Quinolones act, at least in part, by inhibiting synthesis of DNA, thus preventing the cell from replicating.

Many attempts to produce improved antimicrobials yield equivocal results. Indeed, few antimicrobials are produced that are truly clinically acceptable in terms of their spectrum of antimicrobial activity, avoidance of microbial resistance, and pharmacology. There is a continuing need for broad-spectrum antimicrobials, and a particular need for antimicrobials effective against resistant microbes.

Pathogenic bacteria are known to acquire resistance via several distinct mechanisms including inactivation of the antibiotic by bacterial enzymes (e.g., beta-lactamases that hydrolyze penicillin and cephalosporins); removal of the antibiotic using efflux pumps; modification of the target of the antibiotic via mutation and genetic recombination (e.g., penicillin-resistance in *Neiserria gonorrhea*); and acquisition of a readily transferable gene from an external source to create a resistant target (e.g., methicillin-resistance in *Staphylococcus aureus*). There are certain Gram-positive pathogens, such as vancomycin-resistant *Enterococcus faecium*, which are resistant to virtually all commercially available antibiotics.

Resistant organisms of particular note include methicillin-resistant and vancomycin-resistant *Staphylococcus aureus*, penicillin-resistant *Streptococcus pneumoniae*, vancomycin-resistant enterococci, fluoroquinolone-resistant *E. coli*, cephalosporin-resistant aerobic gram-negative rods and imipenem-resistant *Pseudomonas aeruginosa*. These organisms are significant causes of nosocomial infections and are clearly associated with increasing morbidity and mortality. The increasing numbers of elderly and immunocompromised patients are particularly at risk for infection with these pathogens. Therefore, there is a large unmet medical need for the development of new antimicrobial agents. In recent years Methicillin Resistant *Staphylococcus Aureus* (MRSA) infections have become more common, particularly in institutional and hospital settings. Up to 60% of *staphylococcus* infections are attributable to methicillin resistant strains in some parts of the United States. Some MRSA strains are now resistant to both Vancomycin and Gentamicin, drugs once considered the last defense against *staphylococcus* infections. Thus, there is a particularly urgent need for drugs effective against MRSA strains.

Quinoline compounds effective against methicillan susceptible *Staphylococcus aureus* have been previously identified. For example, see Japanese laid-open publication no. 03-223289. JP 03-223289 discusses compounds having activity against MSSA rather than MRSA. Generally quinolone and isothiazoloquinolone compounds are 32-128 fold less active against MRSA than MSSA. Thus one of skill in the art would not expect compounds discussed in JP 03-223289 to be effective against MRSA. The inventors have unexpectedly identified a class of hydroxylthienoquinolones that are only 4-8 fold less active against MRSA than MSSA, as measured by MIC assay, and thus quite useful for treating MRSA infections. The unexplained improved MSSA/MRSA MIC ratio also suggests an alternate mode of action or binding at the active site for the newly discovered compounds.

The present invention fulfills the need for drugs effective against MRSA, and provides further related advantages.

SUMMARY OF THE INVENTION

The invention provides hydroxylthienoquinolone compounds of Formula I (shown below) and related compounds. The invention provides compounds of Formula I and related compounds, which possess potent and/or selective antibacterial, antiprotozoal, or antifungal activity. The invention also provides pharmaceutical compositions containing one or more compounds of Formula I or related compounds together with one or more pharmaceutically acceptable carriers.

The invention further comprises methods of treating microbial infections, particularly bacterial and protozoal infections by administering an effective amount of a compound of Formula I or related compound to a patient suffering from a microbial infection. These microbial infections include bacterial infections, for example *E. coli* infections, *Staphylococcus* infections, particularly including Methicillin Resistant *Staphylococcus Aureus* infections, *Salmonella* infections and protozoal infections, for example *Chlamydia* infections. The invention is particularly includes methods of treating microbial infections in mammals, including human patients, but also encompasses methods of treating microbial infections in other animals, including fish, birds, reptiles, and amphibians.

Methods of treatment include administering a compound of Formula I as the single active agent or administering a compound of Formula I in combination with one or more other therapeutic agent, such as an antibacterial, an antifungal, an antiviral, an interferon or other immune system modulator, an efflux-pump inhibitor, a beta-lactamase inhibitor, an anti-inflammatory, or another compound of Formula I.

Thus, compounds of Formula I

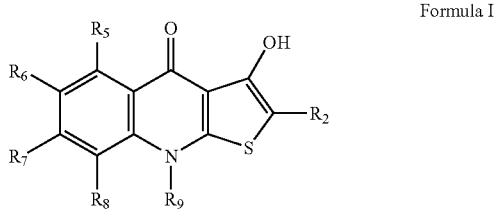

Formula I and the pharmaceutically acceptable salts thereof, are provided herein. Within Formula I, the variables, e.g. $R_2$, $R_5$, $R_6$, $R_7$, $R_8$, and $R_9$, carry the definitions set forth below.

$R_2$ is cyano, amino, nitro, —$COR^b$, —$SO_2R^b$, trifluoromethyl, or phenyl substituted with 0 to 2 substituents independently chosen from halogen, $C_1$-$C_2$alkyl, and $C_1$-$C_2$alkoxy, where $R^b$ is hydroxyl, $C_1$-$C_6$alkoxy, $C_1$-$C_6$alkyl, aryl, aryloxy, —$N(R^a)_2$, or trifluoromethyl; and $R^a$ is independently chosen at each occurrence from hydrogen, $C_1$-$C_6$alkyl, and aryl.

$R_5$ is hydrogen, hydroxyl, halogen, $C_1$-$C_6$alkyl, or $C_1$-$C_6$alkoxy.

$R_6$ is hydrogen or halogen.

$R_7$ is phenyl or a C-linked 5- to 6-membered partially unsaturated heterocyclic group; or $R_7$ is a nitrogen-linked heterocycloalkyl group, which has 1 ring or 2 fused rings, a total of 4 to 8 ring members, including 0, 1, or 2 additional ring heteroatoms independently chosen from N, O, and S, or $R_7$ is a nitrogen-linked 6-membered heterocycloalkyl group, having 0, 1 or 2 additional ring heteroatoms independently chosen from N, O, and S, and bridged with a methylene or ethylene bridge.

Each of which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_2$-$C_6$alkenyl, $C_1$-$C_6$alkoxy, $C_1$-$C_2$haloalkyl, $C_1$-$C_2$haloalkoxy, and amino $C_1$-$C_2$alkyl, and (b) is oxo, amino, —$CONH_2$, $C_1$-$C_4$alkyl substituted with at least one hydroxyl or cyano, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl) ($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, or $R_{10}$—O—N=, where $R_{10}$ is hydrogen or $C_1$-$C_6$alkyl, or $R_{13}R_{14}$C= where $R_{13}$ is halogen and $R_{14}$ is amino$C_1$-$C_4$alkyl; where each of (b) other than oxo, cyano, and —$CONH_2$, is substituted with 0 to 2 substituents independently chosen from halogen, hydroxyl, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

$R_8$ is methoxy or difluoromethoxy.

$R_9$ is $C_1$-$C_4$alkyl, $C_3$-$C_7$cycloalkyl, phenyl, or pyridyl, each of which $R_9$ is substituted with 0 to 3 substituents independently chosen from amino, halogen, $C_1$-$C_4$alkyl, and $C_1$-$C_4$alkoxy.

$R_8$ and $R_9$ are joined to form a 6-membered ring optionally containing one additional heteroatom chosen from N, O, and S, and optionally containing one carbon-carbon double bond.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature.

In certain situations, the compounds of Formula I may contain one or more asymmetric elements such as stereogenic centers, stereogenic axes and the like, e.g. asymmetric carbon atoms, so that the compounds can exist in different stereoisomeric forms. "Formula I" includes compounds and salts of certain subformulae, described herein such as compounds of Formula II to V as well as related compounds of Formula A, B, and C. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $A_1$, $R_2$, $R_3$, $R_5$, $A_6$, $R_7$, $A_8$, and $R_9$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

The term "substituted", as used herein, means that any one or more hydrogen atoms bound to the designated atom or group is replaced with a selection from the indicated group, provided that the designated atom's normal valence is not exceeded. When a substituent is oxo (i.e., =O), then 2 hydrogen atoms on the substituted atom are replaced with a double-bonded oxygen. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

Substituents are named into the ring unless otherwise indicated. A dash ("-") or a double bond ("=") that is not between two letters or symbols indicates the point of attachment for a substituent. For example, —CONH$_2$ is attached through the carbon atom.

As used herein, "alkyl" is includes both branched and straight-chain saturated aliphatic hydrocarbon groups, having the specified number of carbon atoms. Thus, the term $C_1$-$C_6$alkyl as used herein includes alkyl groups having from 1 to about 6 carbon atoms. When $C_0$-$C_r$, alkyl is used herein in conjunction with another group, for example, (aryl)$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, t-butyl, n-pentyl, and sec-pentyl. $C_1$-$C_0$alkyl includes alkyl groups have 1, 2, 3, 4, 5, or 6 carbon atoms.

"Alkenyl" as used herein, indicates a hydrocarbon chain of either a straight or branched configuration having one or more carbon-carbon double bond bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propylamino. A "(mono- and/or di-alkyl)amino$C_0$-$C_4$alkyl group is a mono and/or dialkylamino group as defined that is directly bound to the group it substitutes ($C_0$alkyl) or attached to the group it substitutes via a 1 to 4 carbon alkyl group linker.

"Alkylthio" indicates an alkyl group as defined above attached through a sulfur linkage, i.e. a group of the formula alkyl-S—. Examples include ethylthio and pentylthio.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl. "Aryloxy" is an aryl groups as defined above, attached to the group it substitutes via a covalently bound oxygen atom.

In the term "(aryl)alkyl," aryl and alkyl are as defined above, and the point of attachment is on the alkyl group. This term encompasses, but is not limited to, benzyl, phenylethyl, and piperonyl.

The term "carbocyclic group" indicates a monocyclic or bicyclic saturated, partially unsaturated, or aromatic ring system in which all ring atoms are carbon. Usually each ring of the carbocyclic group contains from 4-6 ring atoms and a bicyclic carbocyclic group contains from 7 to 10 ring atoms but some other number of ring atoms may be specified. Unless otherwise indicated, the carbocyclic group may be attached to the group it substitutes at any carbon atom that results in a stable structure. When indicated the carbocyclic rings described herein may be substituted at any carbon atom if the resulting compound is stable.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane. In the term "(cyclolalkyl)alkyl," cycloalkyl and alkyl are as defined above, and the point of attachment in on the alkyl group. In the term "(cyclolalkyl)amino$C_0$-$C_4$alkyl," cycloalkyl, amino, and alkyl are as defined above, and the point of attachment in on the alkyl group or through a nitrogen bridge ($C_0$alkyl).

"Cycloalkenyl" as used herein, indicates an unsaturated, but not aromatic, hydrocarbon ring having at least one carbon-carbon double bond. Cycloalkenyl groups contain from 4 to about 8 carbon atoms, usually from 4 to about 7 carbon atoms. Examples include cyclohexenyl and cyclobutenyl.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

"Heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

In the term "(heteroaryl)alkyl," heteroaryl and alkyl are as defined above, and the point of attachment is on the alkyl group. These terms include such examples as pyridylmethyl, thiophenylmethyl, and pyrrolyl(1-ethyl).

The term "heterocycloalkyl" indicates a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups.

The term "heterocyclic group" indicates a monocyclic saturated, partially unsaturated, or aromatic ring containing from 1 to about 4 heteroatoms chosen from N, O, and S, with remaining ring atoms being carbon, or a bicyclic saturated, partially unsaturated, or aromatic heterocylic ring system containing at least 1 heteroatom in the two ring system chosen from N, O, and S and containing up to about 4 heteroatoms independently chosen from N, O, and S in each ring of the two ring system. Usually each ring of the heterocyclic group contains from 4-6 ring atoms but some other number of ring atoms may be specified. Unless otherwise indicated, the heterocyclic ring may be attached to its pendant group at any heteroatom or carbon atom that results in a stable structure. When indicated the heterocyclic rings described herein may be substituted on carbon or on a nitrogen atom if the resulting compound is stable. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

As used herein "active agents" are compounds that have pharmaceutical utility, e.g. may be used to treat a patient suffering from a disease or condition, or may be used prophylacticly to prevent the onset of a disease or condition in a patient, or that may be used to enhance the pharmaceutical activity of other compounds.

"Pharmaceutical compositions" are compositions comprising at least one active agent, such as a compound or salt of Formula I and at least one other excipient. "Carriers" are any inactive materials, including excipients and diluents, that may be added to the pharmaceutical compositions including carriers and diluents. Pharmaceutical compositions meet the U.S. FDA's GMP (good manufacturing practice) standards for human or non-human drugs.

"Salts" of the compounds of the present invention include inorganic and organic acid and base addition salts. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

"Pharmaceutically acceptable salts" includes derivatives of the disclosed compounds wherein the parent compound is modified by making non-toxic acid or base salts thereof, and further refers to pharmaceutically acceptable hydrates solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "therapeutically effective amount" of a compound of Formula I, or a related formula, means an amount effective, when administered to a human or non-human patient, to provide a therapeutic benefit such as an amelioration of symptoms, e.g., an amount effective to decrease the symptoms of a microbial infection, and including an amount sufficient to reduce the symptoms of a bacterial, fungal, or protozoal infection. In certain circumstances a patient suffering from a microbial infection may not present symptoms of being infected. Thus a therapeutically effective amount of a compound is also an amount sufficient significantly reduce the detectable level of microorganism or antibodies against the microorganism in the patient's blood, serum, other bodily fluids, or tissues. The invention also includes, in certain embodiments, using compounds of Formula I in prophylactic treatment and therapeutic treatment. In the context of prophylactic or preventative treatment a "therapeutically effective amount" is an amount sufficient to significantly decrease the treated patients risk of contracting a microorganism infection. For example, prophylactic treatment may be administered when a subject will knowingly be exposed to infectious microbes. A significant reduction is any detectable negative change that is statistically significant in a standard parametric test of statistical significance such as Student's T-test, where $p<0.05$.

Antimicrobial Compounds

In addition to compounds the compounds of Formula I described above, the invention also includes the following embodiments.

The invention includes compounds and salts of the Formula I

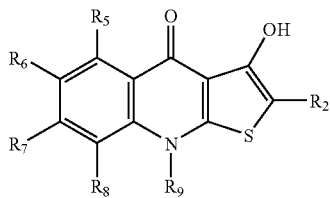

Formula I as described in the Summary of Invention section.

Included herein are compounds of the Formula A in keto and enol form. All possible tautomers are included.

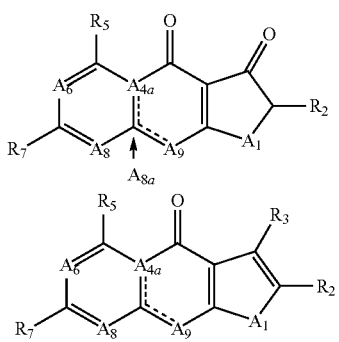

Formula A

In Formula A the variables $A_1$, $R_2$, $R_3$, $R_5$, $R_6$, $R_7$, $A_8$, and $R_9$ carry the values set forth below.

$A_1$ is S, O, or $NR^a$, where $R^a$ is independently chosen at each occurrence from hydrogen, $C_1$-$C_6$alkyl, and aryl; and $R_2$ is halogen, cyano, nitro, —$COR^b$, —$SO_2R^b$, —$N(C_1$-$C_6$alkyl$)_3^+$, trifluoromethyl, or phenyl, each of which is substituted with 0 or 2 substituents independently chosen from halogen, $C_1$-$C_2$alkyl, or $C_1$-$C_2$alkoxy, where $R^b$ is hydroxyl, $C_1$-$C_6$alkoxy, $C_1$-$C_6$alkyl, aryl, aryloxy, —$N(R^a)_2$ or trifluoromethyl.

$R_3$ is hydroxyl or thiol.

$A_{4a}$ is N or C.

When $A_{4a}$ is N, $A_9$ is $CR^d$ and the double bond is between the $A_{8a}$ and $A_9$ position.

When $A_{4a}$ is C, $A_9$ is $NR^f$ and the double bond is between the $A_{4a}$ and $A_{8a}$ position.

$R_5$ is hydrogen, hydroxyl, halogen, $C_1$-$C_6$alkyl, $C_1$-$C_6$alkoxy, aryloxy, aryl, —$N(R^a)_2$, or —$N$=$NR^a$.

$A_6$ is N or $CR^c$, where $R^c$ is hydrogen, halogen, hydroxyl, $C_1$-$C_6$alkyl, $C_1$-$C_6$alkoxy, aryloxy, aryl, $C_1$-$C_2$haloalkyl, $C_1$-$C_2$haloalkoxy, or —$N(R^a)_2$.

$R_7$ is $XR^E$.

X is absent, —$CH_2$—$CH_2$—, —$CH$=$CH$—, —(C=O)—, —(C=O)NH—, or —$C$≡$C$—.

$R^E$ is $C_3$-$C_7$cycloalkyl, $C_4$-$C_7$cycloalkenyl, phenyl, a 7-10 membered bicyclic saturated, partially unsaturated, or aromatic carbocyclic group, a C-linked 5-6-membered heterocyclic group, or C-linked 7-10 membered bicyclic heterocylic group.

$R_7$ is a nitrogen-linked heterocycloalkyl group, which has 1 ring or two fused rings, a total of 4 to 8 ring members, including 0, 1, or 2 additional ring heteroatoms independently chosen from N, O, and S, or $R_7$ is a nitrogen-linked $C_1$-$C_4$alkylamino substituted with a 5- or 6-membered heteroaryl group having 1 or 2 heteroatoms independently chosen from N, O, and S, or substituted with a heterocycloalkyl group, which has 4 to 8 ring members, including 1 or 2 ring heteroatoms independently chosen from N, O, and S, or $R_7$ is a nitrogen-linked heterocycloalkyl or heterocycloalkenyl ring, each of which ring has 4 to 8 ring members, including 0, 1, or 2 additional ring heteroatoms independently chosen from N, O, and S, forming part of a bicyclic system with a 3- to 8-membered cycloalkyl or heterocycloalkyl ring in fused or spiro orientation; or $R_7$ is a nitrogen-linked 6-membered heterocycloalkyl ring, 0, 1 or 2 additional ring heteroatoms independently chosen from N, O, and S, and bridged with a methylene or ethylene bridge.

Each of which $R_7$ is substituted with 0 or 1 or more substituents independently chosen from (a) and 0 or 1 substituents chosen from (b). Wherein (a) is chosen from halogen, hydroxyl, amino, nitro, $C_1$-$C_6$alkyl, $C_2$-$C_6$alkenyl, $C_1$-$C_6$alkoxy, $C_1$-$C_2$haloalkyl, $C_1$-$C_2$haloalkoxy, and amino$C_1$-$C_2$alkyl, and (b) is oxo, amino, cyano, —$CONH_2$, $C_1$-$C_4$alkyl substituted with at least one hydroxyl, amino or cyano, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl) ($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, or $R_{10}$—O—N=, where $R_{10}$ is hydrogen, $C_1$-$C_6$alkyl, ($C_3$-$C_7$cycloalkyl)$C_0$-$C_2$alkyl, or (phenyl)$C_0$-$C_2$alkyl, where each of (b) other than oxo and cyano is substituted with 0 to 2 substituents independently chosen from halogen, hydroxyl, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy.

$A_8$ is N or $CR^x$; where $R^x$ is hydrogen, halogen, hydroxyl, cyano, $C_1$-$C_6$alkyl, $C_1$-$C_6$alkoxy, aryloxy, aryl, $C_1$-$C_2$haloalkyl, $C_1$-$C_2$haloalkoxy, or —$N(R^a)_2$.

$A_9$ is $NR^f$ or $CR^d$, where $R^d$ is $C_1$-$C_6$alkyl, $C_3$-$C_7$cycloalkyl, or aryl and $R^f$ is $C_1$-$C_6$alkyl, $C_3$-$C_7$cycloalkyl, aryl, or substituted heteroaryl. Formula A includes compounds in which $A_8$ is $CR^x$ and $A_9$ is $NR^f$ and $R^x$ and $R^f$ are joined to form an optionally substituted 6 membered ring containing no additional heteroatoms or 1 oxygen atom. Formula I also includes compounds in which $A_x$ is $CR^x$ and $A_9$ is $CR^d$.

The invention also includes compounds of Formula I in which certain variables carry the definitions set forth below. Variables for which a definition is not specified carry the definition set forth for compounds of Formula I in the Summary of Invention section. Compounds may carry any combination of the variable definitions disclosed herein, so long s $A_1$ is O or $NR^a$, where $R^a$ is independently chosen at each occurrence from hydrogen, $C_1$-$C_6$alkyl, and aryl.

$A_1$ in certain embodiments is S and $R_2$ is halogen, $-SO_2R^b$, or $-N(C_1$-$C_6$alkyl$)_3^+$, where $R^b$ is hydroxyl, $C_1$-$C_6$alkyl, $C_1$-$C_6$alkoxy, aryloxy, aryl, $N(R^a)_2$, or trifluoromethyl, where $R^a$ is hydrogen, $C_1$-$C_6$alkyl, or aryl.

In certain embodiments $A_1$ is S, $R_2$ is halogen, $-SO_2R^b$, or $-N(C_1$-$C_6$alkyl$)_3^+$, where $R^b$ is hydroxyl, $C_1$-$C_6$alkyl, $C_1$-$C_6$alkoxy, aryloxy, aryl, $N(R^a)_2$, or trifluoromethyl, where $R^a$ is hydrogen, $C_1$-$C_6$alkyl, or aryl, and $A_9$ is N or $CR^i$; wherein $R^i$ is $C_2$-$C_6$alkyl, (aryl)$C_0$-$C_4$alkyl, or haloalkoxy.

The invention includes compounds and salts of Formula B

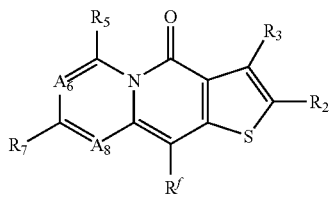

Formula B

Within Formula B the following conditions are met.

$R_2$ is halogen, cyano, nitro, $-COR^b$, $-SO_2R^b$, $-N(C_1$-$C_6$alkyl$)_3^+$, trifluoromethyl, or phenyl substituted with 0 to 2 substituents, independently chosen from halogen, $C_1$-$C_2$alkyl, or $C_1$-$C_2$alkoxy where $R^b$ is hydroxyl, $C_1$-$C_6$alkoxy, $C_1$-$C_6$alkyl, aryl, aryloxy, $-N(R^a)_2$, or trifluoromethyl; and $R^a$ is independently chosen at each occurrence from hydrogen, $C_1$-$C_6$alkyl, and aryl.

$R_3$ is hydroxyl or thiol.

$R^f$ is $C_1$-$C_6$alkyl, $C_3$-$C_7$cycloalkyl, aryl, or substituted heteroaryl.

The remaining variables, e.g. $R_5$, $A_6$, $R_7$, and $A_8$ carry the definitions set forth in Formula A.

The invention includes compounds and salts of Formula C and Formula II

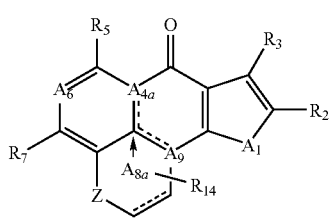

Formula C

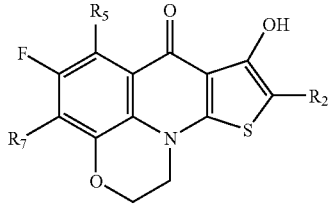

Formula II

Within Formula I the following conditions are met.

$A_1$ is S, O, or $NR^a$, where $R^a$ is independently chosen at each occurrence from hydrogen, $C_1$-$C_6$alkyl and aryl.

$R_2$ is cyano, nitro, halogen, $-COR^b$, $-SO_2R^b$, $N(C_1$-$C_6$alkyl$)_3^+$, trifluoromethyl, or phenyl substituted with 0 to 2 substituents independently chosen from halogen, $C_1$-$C_2$alkyl, or $C_1$-$C_2$alkoxy, where $R^b$ is hydroxyl, $C_1$-$C_6$alkyl, $C_1$-$C_6$alkoxy, aryloxy, aryl, $-N(R^a)_2$, or trifluoromethyl.

$R_3$ is hydroxyl or thiol.

$A_{4a}$ is N or C, when $A_{4a}$ is N, $A_9$ is C and the double bond is between the $A_{8a}$ and $A_9$ position, and when $A_{4a}$ is C, $A_9$ is N and the double bond is between the $A_{4a}$ and $A_{8a}$ position.

$A_9$ is N or C.

Z is O or $CHR_{11}$, where $R_{13}$ is hydrogen, halogen, or $C_1$-$C_6$alkyl.

$R_{14}$ is 0 to 2 substituents independently chosen from halogen, $C_1$-$C_2$alkoxy, and $C_1$-$C_2$alkyl.

The remaining variables including $R_5$, $A_6$, and $R_7$ carry the definitions set forth for compounds of Formula I, or any of the other definitions set forth herein for these variables.

The invention includes compounds and salts of Formula IV and Formula V (both tautomers are included):

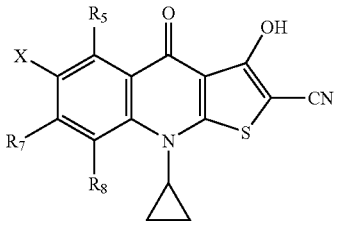

Formula III

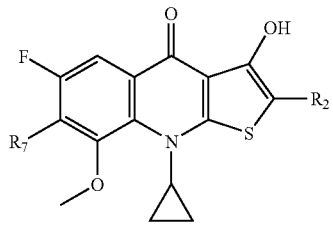

Formula IV

Within Formula III and IV the variables X, $R_5$, $R_6$, $R_7$, $R_8$, and $R_9$ carry the following definitions. These variables may also carry any of the definitions set forth herein.

$R_5$ is hydrogen, hydroxyl, halogen, $C_1$-$C_2$alkyl, or $C_1$-$C_2$alkoxy.

X is halogen.

$R_7$ is phenyl or pyridyl, or $R_7$ is a nitrogen-linked heterocycloalkyl group, which has 1 ring or 2 fused rings, a total of 4 to 8 ring members, including 0, 1, or 2 additional ring heteroatoms independently chosen from N, O, and S.

Each of which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_2$-$C_6$alkenyl, $C_1$-$C_6$alkoxy, $C_1$-$C_2$haloalkyl, $C_1$-$C_2$haloalkoxy, and amino$C_1$-$C_2$alkyl, and (b) is oxo, amino, cyano, —$CONH_2$, $C_1$-$C_4$alkyl substituted with at least one hydroxyl, amino or cyano, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, or $R_{10}$—O—N=, where $R_{10}$ is hydrogen, $C_1$-$C_6$alkyl, ($C_3$-$C_7$cycloalkyl)$C_0$-$C_2$alkyl, or (phenyl)$C_0$-$C_2$alkyl, where each of (b) other than oxo, cyano, and —$CONH_2$, is substituted with 0 to 2 substituents independently chosen from halogen, hydroxyl, amino, cyano, nitro, oxo, —COOH, —$CONH_2$, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_8$ is cyano, methoxy, or difluoromethoxy.

The invention also includes compounds and salts for Formula I in which one or more of the variables carry the definitions set forth below. Compounds of Formula I having any combination of the variable definitions described herein are within the scope of the invention so long as a stable compound results.

The $R_2$ Variable $R_2$ may carry any of the following values.

$R_2$ is cyano, —$CONH_2$, or —$COR^b$, where $R^{bb}$ is $C_1$-$C_2$alkyl or $C_1$-$C_2$alkoxy; and $R_5$ is hydrogen.

$R_2$ is cyano, nitro, —$COR^b$, or trifluoromethyl.

$R_2$ is cyano, —$CONH_2$, or acetyl.

$R_2$ is cyano.

$R_2$ is acetyl.

$R_2$ is fluoro, —$SO_2R^b$, —$N(C_1$-$C_6$alkyl$)_3^+$, or where $R^b$ is hydroxyl, $C_1$-$C_2$alkoxy, $C_1$-$C_2$alkyl, or phenyl.

The $R_5$ and $A_6$ Variables $R_5$ and $A_6$ may carry any of the following definitions.

$R_5$ is hydrogen.

$A_6$ is $CR^c$ and $R^c$ is hydrogen or halogen.

$R_5$ is hydrogen and $R_6$ is fluoro.

$R_6$ is halogen.

$R_6$ is fluoro.

The $R_7$ Variable $R_7$ may carry any of the following definitions.

(1) In certain embodiments $R_7$ is

The following definitions apply to the above table.

$R^g$ is hydrogen or $C_1$-$C_4$alkyl and $R^h$ is hydrogen or $C_1$-$C_6$alkyl, alternatively $R^g$ is $C_1$-$C_4$alkyl and $R^h$ is hydrogen or $C_1$-$C_6$alkyl.

$R^k$ is independently hydrogen, or $C_1$-$C_6$alkyl, wherein $R^g$, and $R^h$ and $R^k$, when other than hydrogen, are substituted with 0 to 2 substituents independently chosen from halogen, hydroxyl, amino, cyano, and $C_1$-$C_2$alkoxy.

$R_m$ is $C_1$-$C_2$alkyl or piperazine.

$R_p$ is hydroxyl, amino, or $C_1$-$C_2$alkyl substituted with one hydroxyl, amino, or cyano substituent.

$R_q$ is amino, ($C_1$-$C_4$alkyl)amino$C_1$-$C_2$alkyl, amino$C_1$-$C_2$alkyl, —$CONH_2$, trifluoromethyl, or triazolyl.

$R_x$ is hydrogen or halogen.

One of $R_y$ and $R_z$ is halogen and the other is amino$C_1$-$C_4$alkyl.

n is an integer from 3 to 7 and v is 1, 2, or 3.

$R_{11}$ is amino or amino$C_1$-$C_4$alkyl and $R_{12}$ is hydrogen, amino$C_1$-$C_4$alkyl, or $R_{11}$ and $R_{12}$ are joined to form a 3 to 5 membered cycloalkyl group or a 3 to 5 membered heterocycloalkyl group having a single nitrogen atom.

(2) In other embodiments $R_7$ is

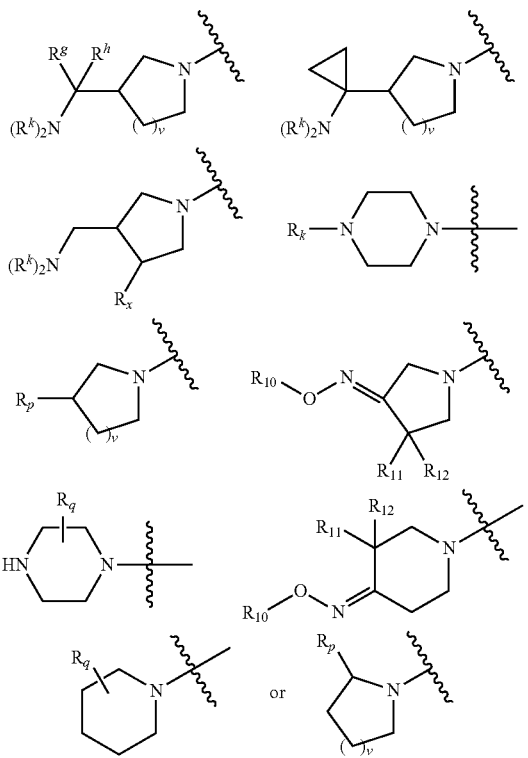

$R^g$ is hydrogen or $C_1$-$C_4$alkyl and $R^h$ is hydrogen or $C_1$-$C_6$alkyl.

$R^k$ is independently hydrogen, or $C_1$-$C_6$alkyl, wherein $R^g$, and $R^h$ and $R^k$, when other than hydrogen, are substituted with 0 to 2 substituents independently chosen from halogen, hydroxyl, amino, cyano, and $C_1$-$C_2$alkoxy.

$R_p$ is hydroxyl, amino, or $C_1$-$C_2$alkyl substituted with one hydroxyl, amino, or cyano substituent.

$R_q$ is amino, ($C_1$-$C_4$alkyl)amino$C_1$-$C_2$alkyl, amino$C_1$-$C_2$alkyl, —$CONH_2$, trifluoromethyl, or triazolyl and $R_x$ is halogen.

(3) $R_7$ is

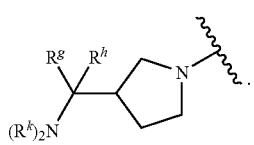

(4) $R_7$ is

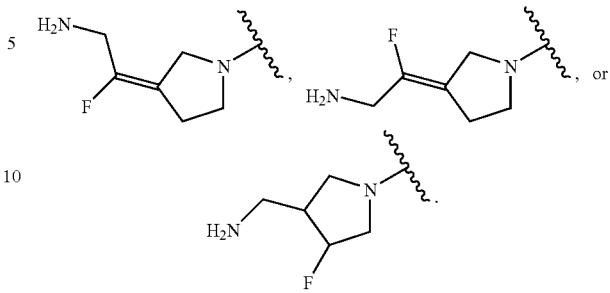

(5) $R_7$, may also be, a nitrogen-linked heterocycloalkyl group, which has 1 ring or two fused rings, a total of 4 to 8 ring members, including 0, 1, or 2 additional ring heteroatoms independently chosen from N, O, and S, which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_1$-$C_6$alkoxy, and amino($C_1$-$C_2$alkyl);

(b) is chosen from oxo, cyano, $C_1$-$C_4$alkyl substituted with at least one hydroxyl or cyano, $C_1$-$C_6$alkylthio, $C_2$-$C_4$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl) ($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, $R_{10}$—O—N═, where $R_{10}$ is hydrogen or $C_1$-$C_6$alkyl, and $R_{13}R_{14}C$═, where $R_{13}$ is fluoro and $R_{14}$ is amino$C_1$-$C_2$alkyl.

Where each of (b) other than oxo, —$CONH_2$, and cyano is substituted with 0 to 2 substituents independently chosen from halogen, hydroxyl, amino, cyano, nitro, oxo, —COOH, —$CONH_2$, $C_1$-$C_4$alkyl, $C_2$-$C_4$alkenyl, $C_1$-$C_4$alkoxy, mono- and di-($C_1$-$C_4$alkyl)amino, $C_1$-$C_2$haloalkyl, and $C_1$-$C_2$haloalkoxy.

(6) $R_7$ is a nitrogen-linked heterocycloalkyl group, which has one ring of 4 to 6 ring members and in which the only additional heteroatoms are 0 or 1 Nitrogen atoms; which $R_7$ is substituted with 0, 1, or 2 substituents independently chosen from (a) and 0 or 1 substituents chosen from (b); wherein:

(a) is chosen from hydroxyl, amino, $C_1$-$C_2$alkyl, $C_1$-$C_2$alkoxy, trifluoromethyl, and amino($C_1$-$C_2$alkyl), and (b) is chosen from —$CONH_2$ $C_1$-$C_4$alkyl substituted with at least one cyano, triazolyl, (mono- and di-$C_1$-$C_4$alkyl)amino$C_0$-$C_4$alkyl, $R_{10}$—O═N—, where $R_{10}$ is hydrogen or $C_1$-$C_2$alkyl, and $R_{13}R_{14}C$═ where $R_{13}$ is fluoro and $R_{14}$ is aminomethyl, where each (b) other than —$CONH_2$ is substituted with 0 to 2 substituents independently chosen from halogen and cyano.

(7) $R_7$ is a nitrogen-linked heterocycloalkyl ring, which ring has 4 to 8 ring members, which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_2$-$C_6$alkenyl, $C_1$-$C_6$alkoxy, $C_1$-$C_2$haloalkyl, and $C_1$-$C_2$haloalkoxy, and (b) is oxo, amino, cyano, —$CONH_2$, $C_1$-$C_4$alkyl substituted with at least one hydroxyl, amino, or cyano, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-C4alkyl, ($C_3$-$C_7$cycloalkyl)amino$C_0$-$C_4$alkyl, ($C_3$-$C_7$cycloalkyl) ($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, or $R_{10}$—O—N═, where $R_{10}$ is hydrogen, $C_1$-$C_6$alkyl, ($C_3$-$C_7$cycloalkyl)$C_0$-$C_2$alkyl, or (phenyl)$C_0$-$C_2$alkyl.

Each (b) other than oxo, cyano, and —CONH$_2$ is substituted with 0 to 2 substituents independently chosen from halogen, hydroxyl, amino, cyano, nitro, oxo, —COOH, —CONH$_2$, C$_1$-C$_4$alkyl, C$_2$-C$_4$alkenyl, C$_2$-C$_4$alkynyl, C$_1$-C$_4$alkoxy, mono- and di-(C$_1$-C$_4$alkyl)amino, C$_1$-C$_2$haloalkyl, and C$_1$-C$_2$haloalkoxy.

(8) R$_7$ is a nitrogen-linked heterocycloalkyl ring, which has 4 to 6 ring members and in which the only additional heteroatoms are 0 or 1 Nitrogen atoms; which R$_7$ is substituted with 0, 1, or 2 substituents independently chosen from (a) and 0 or 1 substituents chosen from (b); wherein (a) is chosen from halogen, hydroxyl, C$_1$-C$_2$alkyl, C$_1$-C$_2$alkoxy, trifluoromethyl, and difluoromethoxy, and (b) is chosen from amino, cyano, —CONH$_2$, C$_1$-C$_4$alkyl substituted with at least one hydroxyl, amino, or cyano, and mono- and di-C$_1$-C$_4$alkyl) amino.

(9) R$_7$ is phenyl, triazolyl, pyridyl, or tetrahydropyridyl; or R$_7$ is a nitrogen-linked 6-membered heterocycloalkyl group, 0, 1 or 2 additional ring heteroatoms independently chosen from N, O, and S, and bridged with a methylene or ethylene bridge.

Each of which R$_7$ is substituted with 0 or 1 or more substituents independently chosen from (a) and 0 and 1 substituents chosen from (b); wherein (a) is chosen from halogen, hydroxyl, amino, C$_1$-C$_2$alkyl, C$_1$-C$_2$alkoxy, trifluoromethyl, trifluoromethoxy, and aminoC$_1$-C$_2$alkyl, and (b) is chosen from oxo, C$_1$-C$_4$alkyl substituted with at least one hydroxyl or cyano, (mono- or di-C$_1$-C$_4$alkyl)aminoC$_0$-C$_4$alkyl, and piperidinyl.

The A$_{4a}$, A$_8$, and A$_9$ Variables

The variables A$_9$ and A$_{4a}$ may carry any of the following definitions.

(1) A$_9$ is NR$^f$ and R$^f$ is substituted heteroaryl.

(2) A$_{4a}$ is C, A$_9$ is NR$^f$ and the double bond is between the A$_{4a}$ and A$_{8a}$ position.

(3) A$_9$ is CR$^x$, where IV is hydrogen, halogen, C$_1$-C$_2$alkoxy, or C$_1$-C$_2$haloalkoxy.

(4) A$_9$ is CR$^x$, where IV is hydrogen or methoxy.

(5) A$_6$ is R$^c$ and R$_8$ is R$^x$.

(6) A$_6$ is CR$^c$ where R$^c$ is hydrogen or fluoro and A$_8$ is C—OCH$_3$.

(7) R$^9$ is methoxy and R$_9$ is cyclopropyl.

(8) A$_9$ is NR$^f$, where R$^f$ is cyclopropyl or pyridyl substituted with halogen and amino.

(9) A$_9$ is cyclopropyl.

Any of the above variable definitions may be combined for a compound of Formula I or any of the subformulae thereof, so long as a stable compound results.

Compounds having improved cytotoxicity are provided herein. For example, compounds in which R$_2$ is acetyl exhibit surprisingly low cellular toxicity compared to other compound of Formula I and other structurally similar compounds. For example certain compounds provided herein exhibit suprisingly low cytotoxicity in the assay of Example 14.

Compounds, which are potent inhibitors of MRSA are provided herein. For example certain compounds provided herein are potent inhibitors of *S. aureus* strains 700699, BSA643, and BSA648, NY2746.

Anti-Microbial and Pharmaceutical Preparations

The invention provides pharmaceutical compositions, comprising a compound or salt thereof of Formula I, together with at least one pharmaceutically acceptable excipient.

Compounds described herein can be administered as the neat chemical, but are specifically administered as a pharmaceutical composition, for example compounds can be administered a pharmaceutical formulation compound of Formula I or related compound of Formula II to V or a or pharmaceutically acceptable salt thereof, together with at least one pharmaceutically acceptable carrier.

The compounds described herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, an injectable fluid, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorings, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active and/or inactive agents may be included in the pharmaceutical compositions, provided that such agents do not substantially interfere with the activity of the Aryl substituted thiazol-2-yl-piperidines and related compounds used in the pharmaceutical compositions. The optional active is an additional active agent that is not a compound or salt of Formula I or Formula II.

The pharmaceutical compositions can be formulated for oral administration. These compositions contain between 0.1 and 99 weight % (wt. %) of a compound of Formula I or related compound or salt and usually at least about 5 wt. % of a compound or salt of Formula I Some embodiments contain from about 25 wt. % to about 50 wt. % or from about 5 wt. % to about 75 wt. % of the compound or salt of Formula I or related compound.

Amount of compound or salt of Formula I in a unit dose may be generally varied or adjusted from about 1.0 milligram to about 1,000 milligrams, from about 1.0 to about 950 milligrams, from about 1.0 to about 500 milligrams, or from about 1 to about 250 milligrams, according to the particular application and the potency of the compound. The actual dosage employed may be varied depending upon the patient's age, sex, weight and severity of the condition being treated.

Packaged Formulations

The invention includes packaged pharmaceutical formulations. Such packaged formulations include a pharmaceutical composition containing one or more compounds or salts of Formula I in a container and instructions for using the composition to treat an animal (typically a human patient) suffering from a microorganism infection) or prevent a microorganism infection in an animal.

The instructions may also be instructions for using the composition to treat a patient suffering from a bacterial infection, such as a *S. aureus* infection, including MRSA infection.

In all of the foregoing the compounds of the invention can be administered alone or as mixtures, and the compositions may further include additional drugs or excipients as appropriate for the indication.

Methods of Treatment

The invention includes methods of treating microorganism infections, particularly bacterial and protozoal infections, by administering an effective amount of one or more compounds of Formula I to an patient at risk for a microorganism infection or suffering from a microorganism infection. Treatment of human patients is particularly contemplated. However, treatment of non-human patients is within the scope of the invention. The invention includes treatment or prevention of microbial infections in fish, amphibians, reptiles or birds, but is the invention includes treating mammals. Methods of treating microorganism infections in livestock animals, companion animals, and human patients are particularly preferred.

The compounds disclosed herein are useful for treating bacterial infections in animals. Furthermore compounds of the invention may be used to treat a variety of conditions not attributed to bacterial infections. These include diseases and disorders caused fungal infections, mycoplasma infections, protozoal infections, or other conditions involving infectious organisms.

In some circumstances an effective amount of a compound of Formula I may be an amount sufficient to reduce the symptoms of the microorganism infection. Alternatively an effective amount of a Compound of Formula I may be an amount sufficient to significantly reduce the amount of microorganism or antibodies against the detectable in a patient's tissues or bodily fluids.

Methods of treatment also include inhibiting microorganism replication in vivo, in an animal at risk for a microorganism infection or suffering from such an infection, by administering a sufficient concentration of a compound of Formula I to inhibit bacterial survival in vitro. By "sufficient concentration" of a compound administered to the patient is meant the concentration of the compound available in the animal's system to prevent or combat the infection. Such a concentration by be ascertained experimentally, for example by assaying blood concentration of the compound, or theoretically, by calculating bioavailability. The amount of a compound sufficient to inhibit bacterial survival in vitro may be determined with a conventional assay for bacterial survival such as the Minimum Inhibitory Concentration (MIC) Assay disclosed in Example 2, which follows.

The invention also includes using compounds of Formula I in prophylactic therapies. In the context of prophylactic or preventative treatment an effective amount of a compound of the invention is an amount sufficient to significantly decrease the treated animal's risk of contracting a microorganism infection.

Compounds of the invention are particularly useful for treating infectious disorders. These include for example: ocular infections such as conjunctivitis; urinary tract and genital infections, such as complicated urinary tract infections, acute urinary tract and genital infections, such as pyelonephritis, cervical gonococcal infections, cystitis, urethral chlamydial infections, cervical chlamydial infections, urethral gonococcal infections, and prostatitis, respiratory infections, such as lower respiratory tract infections, acute sinusitis, acute exacerbations of chronic bronchitis, community-acquired pneumonia, and nosocomial pneumonia, skin infections, such as skin-structure infections, impetigo, folliculitis, boils, scalded skin syndrome, and cellulites, and other infections such as bone infections, joint infections, infectious diarrhea, typhoid fever, intra-abdominal infections, gynecologic infections, including toxic shock syndrome, pelvic infections, and post-surgical infections. In a preferred embodiment compounds of Formula I are used to treat *Staphylococcus* infections, especially Methicillan Resistant *Staphylococcus aureus* infections.

The disclosed compounds are useful for treating infections caused by the following microorganisms:

Aerobic Gram-positive Microorganisms: Including but not limited to *Enterococcus faecalis, Enterococcus faecium, Staphylococcus aureus* (including methicillin *S. aureus*), *Staphylococcus epidermidis, Staphylococcus saprophyticus, Streptococcus pneumoniae, Streptococcus pyogenes, Staphylococcus haemolyticus,* and *Staphylococcus hominis;*

Aerobic Gram-negative Microorganisms: Including but not limited to *Campylobacter jejuni, Citrobacter diversus, Citrobacter freundii, Enterobacter cloacae, Escherichia coli, Haemophilus influenzae, Haemophilus parainfluenzae, Klebsiella pneumoniae, Moraxella catarrhalis, Morganella morganii, Neisseria gonorrhoeae, Proteus mirabilis, Proteus vulgaris, Providencia rettgeri, Providencia stuartii, Pseudomonas aeruginosa, Stenotrophomonas maltophila, Salmonella typhi, Serratia marcescens, Shigella boydii, Shigella dysenteriae, Shigella flexneri, Shigella sonnei. Acinetobacter Iwoffi, Aeromonas hydrophila, Edwardsiella tarda, Enterobacter aerogenes, Klebsiella oxytoca, Legionella pneumophila, Pasteurella multocida, Salmonella enteritidis, Vibrio cholerae, Vibrio parahaemolyticus, Vibrio* vulnificus, *Yersinia enterocolitica* and *H. Pylori.*

Non-bacterial microorganisms: *Mycoplasma, Legionella* and *Chlamydia.*

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Administration

The compounds of the invention may also be useful in combination with other pharmaceutically active agents such as antibacterial agents, antiviral agents, antifungal agents, anti-inflammatories, interferon, efflux-pump inhibitors, and beta-lactamase inhibitors. Antibiotic agents include any molecule that tends to prevent, inhibit or destroy life and as such, includes anti-bacterial agents, anti-fungicides, anti-viral agents, and anti-parasitic agents.

Pharmaceutical compositions of the invention include single dosage forms containing of a compound of Formula I \ and one or more other active agent, dosage forms containing more than one compound of Formula I, and separate administration of a compound of Formula I with another active agent.

The following active agents, which are useful in combinations of the invention, may be isolated from an organism that produces the agent or synthesized by methods known to those of ordinary skill in the art of medicinal chemistry or purchased from a commercial source.

Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones (see Table below). Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Anti-fungals agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

Antiviral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetyll eucine, Amantadine, Amidinomycin, Delavirdine, Foscarnet, Indinavir, Interferon-α, Interferon-β, Interferon-γ, Kethoxal, Lysozyme, Methisazone, Moroxydine, Nevirapine, Podophyllotoxin, Ribavirin, Rimantadine, Ritonavir, Saquinavir, Stailimycin, Statolon, Tromantadine, and Xenazoic Acid.

Antiinflammatory agents include, but are not limited to, Enfenamic Acid, Etofenamate, Flufenamic Acid, Isonixin, Meclofenamic Acid, Mefenamic Acid, Niflumic Acid, Talniflumate, Terofenamate, Tolfenamic Acid, Aceclofenac, Acemetacin, Alclofenac, Amfenac, Amtolmetin Guacil, Bromfenac, Bufexamac, Cinmetacin, Clopirac, Diclofenac, Etodolac, Felbinac, Fenclozic Acid, Fentiazac, Glucametacin, Ibufenac, Indomethacin, Isofezolac, Isoxepac, Lonazolac, Metiazinic Acid, Mofezolac, Oxametacine, Pirazolac, Proglumetacin, Sulindac, Tiaramide, Tolmetin, Tropesin, Zomepirac, Bumadizon, Butibufen, Fenbufen, Xenbucin, Clidanac, Ketorolac, Tinoridine, Alminoprofen, Benoxaprofen, Bermoprofen, Bucloxic Acid, Carprofen, Fenoprofen, Flunoxaprofen, Flurbiprofen, Ibuprofen, Ibuproxam, Indoprofen, Ketoprofen, Loxoprofen, Naproxen, Oxaprozin, Piketoprofen, Pirprofen, Pranoprofen, Protizinic Acid, Suprofen, Tiaprofenic Acid, Ximoprofen, Zaltoprofen, Difenamizole, Epirizole, Apazone, Benzpiperylon, Feprazone, Mofebutazone, Morazone, Oxyphenbutazone, Phenylbutazone, Pipebuzone, Propyphenazone, Ramifenazone, Suxibuzone, Thiazolinobutazone, Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, I-Naphthyl Salicylate, Olsalazine, Parsalmide, Phenyl Acetylsalicylate, Phenyl Salicylate, Salacetamide, Salicylamide O-Acetic Acid, Salicylsulfuric Acid, Salsalate, Sulfasalazine, Ampiroxicam, Droxicam, Isoxicam, Lornoxicam, Piroxicam, Tenoxicam, epsilon-Acetamidocaproic Acid, S-Adenosylmethionine, 3-Amino-4-hydroxybutyric Acid, Amixetrine, Bendazac, Benzydamine, alpha-Bisabolol, Bucolome, Difenpiramide, Ditazol, Emorfazone, Fepradinol, Guaiazulene, Nabumetone, Nimesulide, Oxaceprol, Paranyline, Perisoxal, Proquazone, Superoxide Dismutase, Tenidap, Zileuton, 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetale, Hydrocortamate, Hydrocortisone, Loteprednol Etabonale, Mazipredone, Medrysone, Meprednisone, Methylprednisolone, Mometasone Furoate, Paramethasone, Prednicarbate, Prednisolone, Prednisolone 25-Diethylaminoacetate, Prednisolone Sodium Phosphate, Prednisone, Prednival, Prednylidene, Rimexolone, Tixocortol, Triamcinolone, Triamcinolone Acetonide, Triamcinolone Benetonide, and Triamcinolone Hexacetonide.

Compounds of the invention may be combined with one or more Beta lactamase inhibitor when used in combination with a beta-lactam class antibiotic, such as penicillin or cephalosporins. Beta-lactamase inhibitors include, but are not limited to Clavulanic acid, Sulbactam, Sultamacillin, and Tazobactam.

Compounds of the invention may also be combined with one or more efflux pump inhibitor, such as a quinazolinone efflux pump inhibitors, d-ornithine-d-homophenylalanine-3-aminoquinoline, Phe-Arg-b-naphthylamide, propafenone, a phenothiazine or thioxanthene efflux pump inhibitor, 1-aza-9-oxafluorenes, N-[4-[2-(3,4-dihydro-6,7-dimethoxy-2(1H)-isoquinolinyl)ethyl]phenyl]-9,10-dihydro-5-methoxy-9-oxo-4-Acridinecarboxamide, reserpine, Milbemycin, Cinchonine, Verapamil, L-phenylalanyl-N-2-naphthalenyl-L-Argininamide (and analogs), 5'-methoxyhydnocarpin-D, methylxanthines, FK506, a cyclosporine efflux pump inhibitor, Nocardamine and other siderophores, Amiodarone, Cyclosporin A, Ro11-2933 (DMDP), Quinidine, and the optical isomers of Propranolol, Quinine (SQ1) and Quinidine, Quinine-10,11-epoxide, Quercetin, Amitriptyline, Taxuspine C derivatives, Emodin, MC-002434; Agosterol A; Pheophorbide; pyridoquinolines such as 2,2'-[(2,8,10-trimethylpyrido [3,2-g]quinoline-4,6-diyl)bis(oxy)]bis[N,N-dimethyl-ethanamine, Gitonavir, and Gemfibrozil.

Synthesis of Compounds

The compounds of the invention are prepared according to methods well-known to those skilled in the art of organic chemical synthesis. The starting materials used in preparing the compounds of the invention are known, made by known methods, or are commercially available.

It is recognized that the skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

In addition, it is recognized that one optical isomer, including a diastereomer and enantiomer, or a stereoisomer, may have favorable properties over the other. When a racemic mixture is discussed herein, it is clearly contemplated to include both optical isomers, including diastereomers and enantiomers, or one stereoisomer substantially free of the other.

This invention is further illustrated by the following examples that should not be construed as limiting.

EXAMPLES

The following abbreviations are used in the reaction schemes and synthetic examples, which follow. This list in not meant to be an all-inclusive list of abbreviations used in the application as additional standard abbreviations, which are readily understood by those skilled in the art of organic synthesis, may also be used in the synthetic schemes and examples.

Aq.—Aqueous
DMF—N,N-Dimethylformamide
DMSO—Dimethyl sulfoxide
rt—Room Temperature
TFA—Trifluoroacetic acid General Methods.

All nonaqueous reactions are performed under an atmosphere of dry argon gas using oven-dried glassware. The progress of reactions is monitored using HPLC and/or thin-layer chromatography (TLC) on glass plates coated with Merck silica gel 60 ($F_{254}$). Flash column chromatography is performed on Merck silica gel 60 (230-400 mesh). All Analytical HPLC is performed using a YMC Pack Pro C18 50×4.6 mm 5 μm column with an isocratic elution of 0.24 min at 90:10 $H_2O$:$CH_3CN$ containing 0.1% TFA followed by a 4-min linear gradient elution from 90:10 to 10:90 at a flow rate of 2.5 mL/min with UV detection at 254 nm. Unless noted otherwise, preparative HPLC is performed using a YMC Pack Pro C18 150×20.0 mm 5 μm column with an isocratic elution of 0.24 min at 97:3 $H_2O$:$CH_3CN$ containing 0.1% TFA followed by a 10-min linear gradient elution from 97:3 to 0:100 at a flow rate of 18.0 mL/min with UV detection at 254 nm. Low-resolution mass spectra are recorded on a Thermo Finnigan Surveyor MSQ instrument (operating in APCI mode) equipped with a Gilson liquid chromatograph. The quasi-molecular ions, [M+H]$^+$, observed in the low-resolution mass spectra are the base peaks. Unless noted otherwise, NMR spectra are recorded at ambient temperature in DMSO-$d_6$ using a Bruker Avance 300 spectrometer (1H at 300.1 MHz, $^{13}C$ at 75.5 MHz, and $^{19}F$ at 282.4 MHz). The chemical shifts for $^1H$ and $^{13}C$ are reported in parts per million (b) relative to external tetramethylsilane and are referenced to signals of residual protons in the deuterated solvent. The chemical shifts for ¹⁹F are reported in parts per million (b) relative to external fluorotrichloromethane. All ¹³C and ¹⁹F NMR spectra are broadband ¹H decoupled.

Example 1

Synthesis of 9-Cyclopropyl-6,7-Difluoro-3-Hydroxyl-8-Methoxy-4-oxo-4,9-dihydrothieno[2,3-b]quinoline-2-carbonitrile

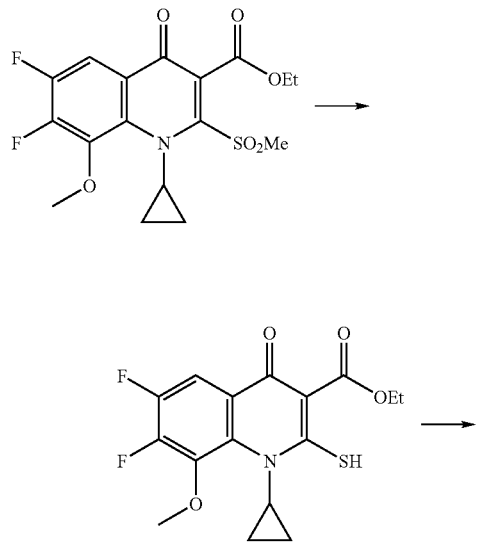

The title compound is prepared from ethyl 1-cyclopropyl-6,7-difluoro-2-mercapto-8-methoxy-4-oxo-1,4-dihydroquinoline-3-carboxylate (See US 2008071086, which is hereby incorporated by reference for its teachings regarding this and other compounds, see also, Hashimoto, et al., 2007) using a procedure analogous to that describing the preparation of 9-cyclopropyl-6,7-difluoro-3-hydroxyl-4-oxo-4,9-dihydrothieno[2,3-b]quinoline-2-carbonitrile. (Chiba, et al., JP 03-223289) The crude product is purified by recrystallization from DMF to give the title compound as a white solid. ¹H NMR: δ 1.04 (m, 2H), 1.27 (m, 2H), 3.90 (m, 1H), 4.02 (d, J=1.5 Hz, 3H), 7.89 (dd, J=10.0 Hz, 8.5 Hz, 1H). ¹⁹F NMR: δ −145.0 (d, J=22.5 Hz, 1F), −138.9 (d, J=22.5 Hz, 1F). LCMS (APCI): m/z calcd for $C_{16}H_{10}F_2N_2O_3S$ ([M]⁺) 348. found 349 ([M+H]⁺).

Example 2

Synthesis of (S)-1-((R)-1-Benzylpyrrolidin-3-yl)-N-(2-fluoroethyl)ethanamine

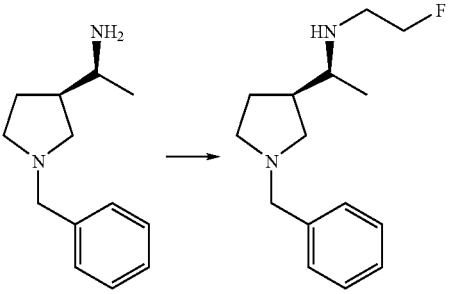

Potassium iodide (0.71 g, 4.27 mmol) and 2-fluoroethyl 4-methylbenzenesulfonate (0.93 g, 4.27 mmol) (Kopka, et al., 2006) are added to a solution of (S)-1-((R)-1-benzylpyrrolidin-3-yl)ethanamine (0.83 g, 4.06 mmol) (Shroeder, et al., 1992) in DMF (10 mL). The reaction mixture is heated for 2 h at 100° C. and evaporated under reduced pressure. The residue is purified by column chromatography (chloroform-ethanol-triethylamine=30:1:1) to afford the desired product (0.51 g, 50%) as a brown oil. ¹H NMR (CDCl₃): δ 1.09 (d, J=6.3 Hz, 3H, methyl), 1.55 (m, 1H), 1.96 (m, 1H), 3.15-2.15 (m, 9H), 3.65 (s, 2H, —CH₂Ph), 4.46 (m, 1H, —CHF), 4.61 (m, 1H, —CHF), 7.31 (m, 5H, ArH). ¹³C NMR (CDCl₃): δ 18.1, 27.5, 43.8, 53.9, 56.7, 57.5, 60.4, 82.4, 84.6, 126.6, 128.1, 128.5, 139.0. LCMS: m/z calcd for $C_{15}H_{23}FN_2$ ([M]⁺) 250. found 251 ([M+H]⁺).

Example 3

Synthesis of 2-fluoro-N—((S)-1-((R)-pyrrolidin-3-yl)ethyl)ethanamine

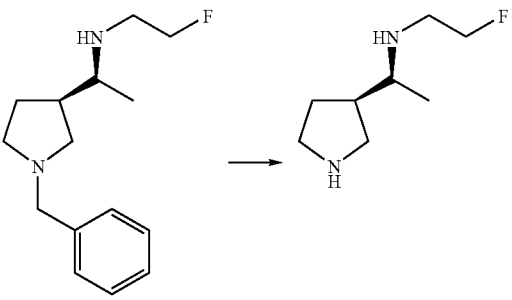

A solution of (S)-1-((R)-1-benzylpyrrolidin-3-yl)-N-(2-fluoroethyl)ethanamine (0.27 g, 1.08 mmol) and palladium hydroxide (0.27 g, 20 wt. % Pd on carbon, 50% wet) in ethanol (8.0 mL) is heated at 40° C. for 15 h under an atmosphere of hydrogen, and cooled to rt. The resulting mixture is filtered through a Büchner funnel on a layer of Celite washing with methanol. The filtrate is evaporated under reduced pressure to afford the title compound in quantitative yield (0.17 g). The residue obtained is used in the next reaction without further purification.

Example 4

Synthesis of 9-cyclopropyl-6-fluoro-7-((R)-3-((S)-1-(2-fluoroethylamino)ethyl)pyrrolidin-1-yl)-3-hydroxyl-8-methoxy-4-oxo-4,9-dihydrothieno[2,3-b]quinoline-2-carbonitrile

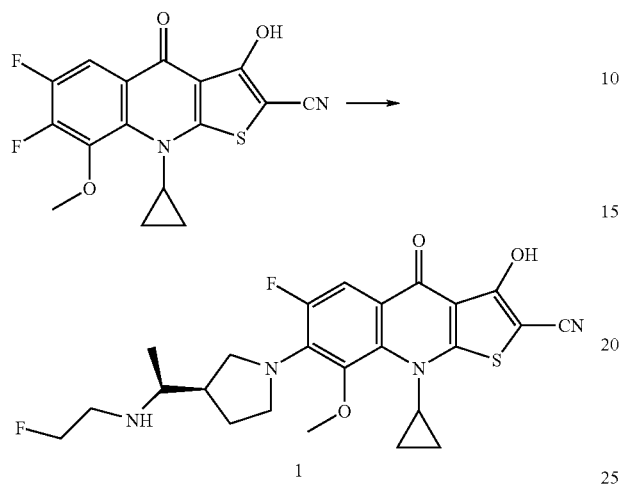

2-Fluoro-N—((S)-1-((R)-pyrrolidin-3-yl)ethyl)ethanamine (0.14 g, 0.87 mmol) and diisopropylethylamine (0.38 mL, 2.18 mmol) are added to a mixture of 9-cyclopropyl-6,7-difluoro-3-hydroxyl-8-methoxy-4-oxo-4,9-dihydrothieno[2,3-b]quinoline-2-carbonitrile (0.15 g, 0.44 mmol) in DMSO (2 mL). The reaction mixture is heated at 110° C. for 18 h, and cooled to rt. The resulting solution is purified by preparative HPLC using mass-based fraction collection to provide the desired mass only fractions. The fractions containing product were combined and lyophilized. The resulting solid was treated with a solution of 1.25 M HCl in methanol (3 mL), evaporated, and triturated with diethyl ether. This step was repeated three times. The brown solid was dissolved in water and lyophilized to afford the desired product (66.1 mg, 29%, HCl salt) as a brown solid.

Example 5

Synthesis of ethyl 1-cyclopropyl-7-fluoro-8-methoxy-2-(methylsulfonyl)-4-oxo-1,4-dihydroquinoline-3-carboxylate

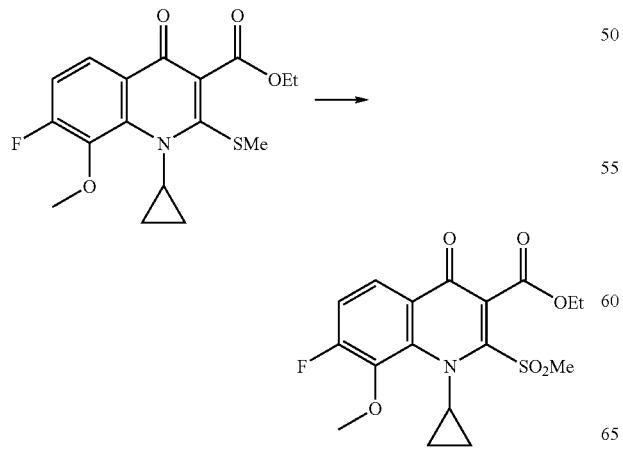

The title compound is prepared from ethyl 1-cyclopropyl-7-fluoro-8-methoxy-2-(methylthio)-4-oxo-1,4-dihydroquinoline-3-carboxylate (See US2007-0049586, which is hereby incorporated for reference for its teachings regarding this compound) using methods analogous to those described previously (treatment with Oxone). (See US 2008071086, and Hashimoto, et al., 2007) $^1$H NMR (CDCl$_3$): δ 0.41 (m, 1H), 0.81 (m, 1H), 1.06 (m, 1H), 1.14-1.31 (m, 1H), 1.40 (t, J=7.5 Hz, 3H), 3.54 (s, 3H), 4.04 (d, J=2.0 Hz, 3H), 4.21 (m, 1H), 4.44 (m, 2H), 7.20 (dd, J=10.5 Hz, 9.0 Hz, 1H), 7.90 (dd, J=9.0 Hz, 5.5 Hz, 1H). $^{19}$F NMR (CDCl$_3$): δ −120.8 (s).

Example 6

Synthesis of 9-cyclopropyl-7-fluoro-3-hydroxyl-8-methoxy-4-oxo-4,9-dihydrothieno[2,3-b]quinoline-2-carbonitrile

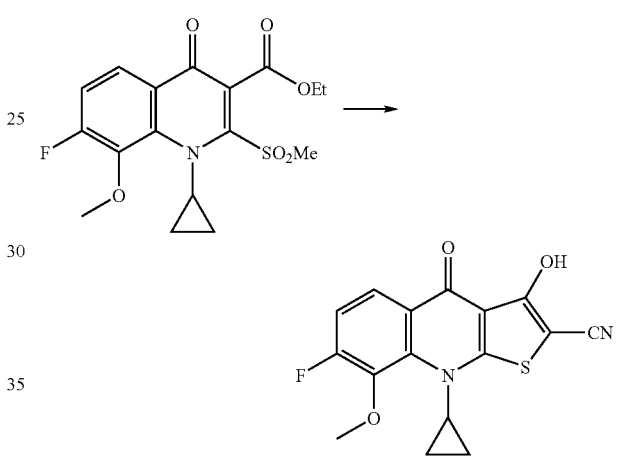

The title compound is prepared from ethyl 1-cyclopropyl-7-fluoro-2-mercapto-8-methoxy-4-oxo-1,4-dihydroquinoline-3-carboxylate using the method described above for the preparation of 9-cyclopropyl-6,7-difluoro-3-hydroxyl-8-methoxy-4-oxo-4,9-dihydrothieno[2,3-b]quinoline-2-carbonitrile. $^1$H NMR: δ1.03 (br, 2H), 1.27 (m, 2H), 3.90 (m, 1H), 3.94 (s, 3H), 7.45 (m, 1H), 8.02 (m, 1H). $^{19}$F NMR: δ−121.70 (s). LCMS: m/z calcd for C$_{16}$H$_{11}$FN$_2$O$_3$S ([M]$^+$) 330. found ([M+H]$^+$) 331.

Example 7

Synthesis of (R)-7-(3-(2-aminopropan-2-yl)pyrrolidin-1-yl)-9-cyclopropyl-3-hydroxyl-8-methoxy-4-oxo-4,9-dihydrothieno[2,3-b]quinoline-2-carbonitrile

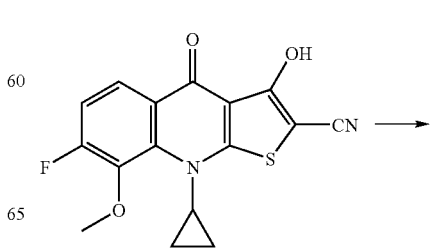

29

-continued

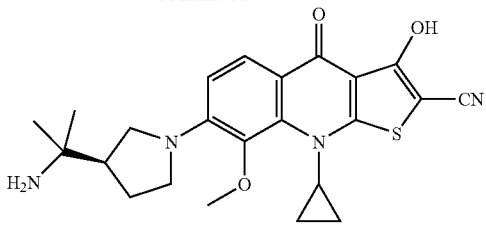

The title compound is prepared from (R)-2-(pyrrolidin-3-yl)propan-2-amine (Fedji, et al., 1994) and 9-cyclopropyl-7-fluoro-3-hydroxyl-8-methoxy-4-oxo-4,9-dihydrothieno[2,3-b]quinoline-2-carbonitrile using the method described above for the preparation of 9-cyclopropyl-6-fluoro-7-((R)-3-(S)-1-(2-fluoroethylamino)ethyl)pyrrolidin-1-yl)-3-hydroxyl-8-methoxy-4-oxo-4,9-dihydrothieno[2,3-b]quinoline-2-carbonitrile.

Example 8

Synthesis of (R)-7-(3-(2-AMINOPROPAN-2-yl)pyrrolidin-1-yl)-9-cyclopropyl-6-fluoro-3-hydroxyl-8-methoxy-4-oxo-4,9-dihydrothieno[2,3-b]quinoline-2-carboxamide

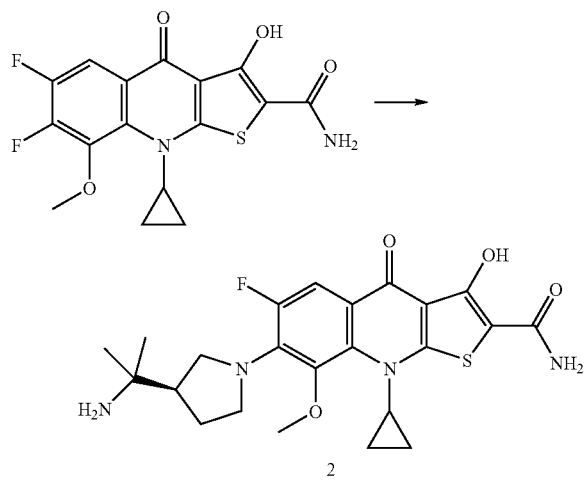

The starting material, 9-cyclopropyl-6,7-difluoro-3-hydroxyl-8-methoxy-4-oxo-4,9-dihydrothieno[2,3-b]quinoline-2-carboxamide, is prepared from ethyl 1-cyclopropyl-6,7-difluoro-2-mercapto-8-methoxy-4-oxo-1,4-dihydroquinoline-3-carboxylate. (See US 2008071086, and Hashimoto, et al., 2007) using a procedure analogous to that describing the preparation of 9-cyclopropyl-6,7-difluoro-3-hydroxyl-4-oxo-4,9-dihydrothieno[2,3-b]quinoline-2-carboxamide. ((Chiba, et al., JP 03-223289) $^1$H NMR: δ 0.98-1.03 (m, 2H), 1.24-1.31 (m, 2H), 3.86-3.93 (m, 1H), 4.04 (d, J=1.5 Hz, 3H), 7.88 (dd, J=10.0 Hz, 8.5 Hz, 1H). $^{19}$F NMR: δ -145.5 (d, J=22.5 Hz, 1F), -139.4 (d, J=22.5 Hz, 1F). LCMS: m/z calcd for $C_{16}H_{12}F_2N_2O_4S$ ([M]$^+$) 366. found ([M+H]$^+$) 367. The title compound is prepared as follows. (R)-2-(Pyrrolidin-3-yl)propan-2-amine (175 mg, 1.4 mmol) is added to a mixture of 9-cyclopropyl-6,7-difluoro-3-hydroxyl-8-methoxy-4-oxo-4,9-dihydrothieno[2,3-b]quinoline-2-carboxamide (100 mg, 0.3 mmol) in pyridine (9 mL). The reaction mixture is heated at 100° C. for 24 h, cooled to rt, and evaporated under reduced pressure. The resulting residue is purified by preparative HPLC using mass-based fraction collection to provide the desired mass only fractions. The fractions containing product were combined and lyophilized. The resulting solid was treated with a solution of 1.25 M HCl in methanol (3 mL), evaporated, and triturated with diethyl ether. This step was repeated three times. The solid was dissolved in water and lyophilized to afford the desired product (40 mg, 29%, HCl salt).

Example 9

Ethyl 1-cyclopropyl-8-(difluoromethoxy)-6-fluoro-2-(methylsulfonyl)-4-oxo-7-(piperazin-1-yl)-1,4-dihydroquinoline-3-carboxylate

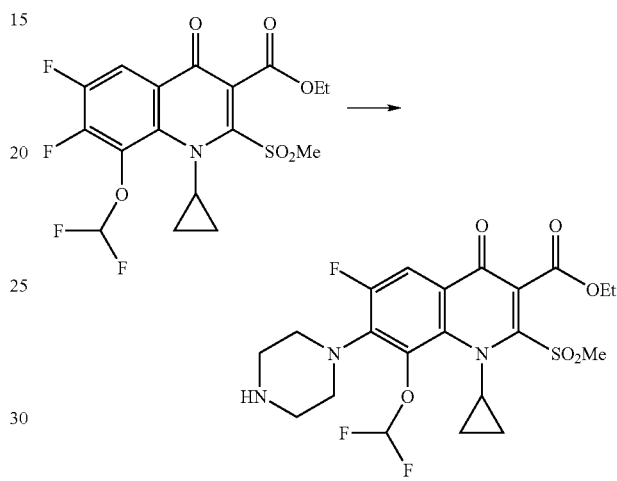

The title compound is prepared from piperazine and ethyl 1-cyclopropyl-8-(difluoromethoxy)-6,7-difluoro-2-(methylsulfonyl)-4-oxo-1,4-dihydroquinoline-3-carboxylate using a procedure analogous to that describing the preparation of (R)-ethyl 7-(3-(2-aminopropan-2-yl)pyrrolidin-1-yl)-1-cyclopropyl-6-fluoro-8-methoxy-2-(methylsulfonyl)-4-oxo-1,4-dihydroquinoline-3-carboxylate. (See US 2008071086, and Hashimoto, et al., 2007) $^1$H NMR (CDCl$_3$): δ 0.30-0.33 (m, 1H), 0.84-0.88 (m, 1H), 0.99-1.04 (m, 1H), 1.20-1.25 (m, 1H), 1.38 (t, J=7.2 Hz, 3H), 2.95-3.21 (m, 6H), 3.44 (s, 3H), 3.51-3.58 (m, 2H), 4.13-4.18 (m, 1H), 4.36-4.48 (m, 2H), 6.54 (dd, J=76.0 Hz, 73.0 Hz, 1H), 7.72 (d, J=12.0 Hz, 1H). $^{19}$F NMR (CDCl$_3$): δ -120.4 (s, 1F), -82.1 (s, 2F). LCMS: m/z calcd for $C_{21}H_{24}F_3N_3O_6S$ ([M]$^+$) 503. found ([M+H]$^+$) 504.

Example 10

9-cyclopropyl-8-(difluoromethoxy)-6-fluoro-3-hydroxyl-4-oxo-7-(piperazin-1-yl)-4,9-dihydrothieno[2,3-b]quinoline-2-carbonitrile

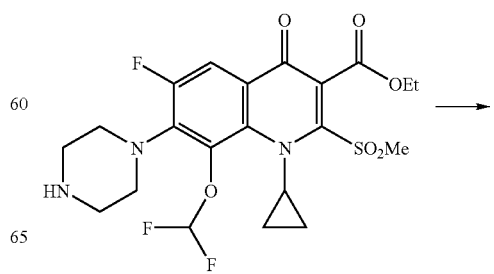

-continued

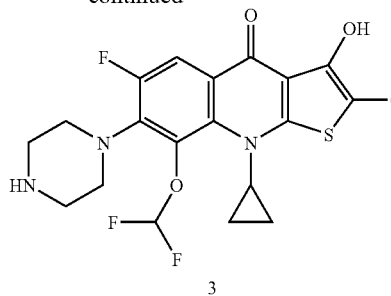

3

The title compound is prepared from ethyl 1-cyclopropyl-8-(difluoromethoxy)-6-fluoro-2-mercapto-4-oxo-7-(piperazin-1-yl)-1,4-dihydroquinoline-3-carboxylate using the method described above for the preparation of 9-cyclopropyl-6,7-difluoro-3-hydroxyl-8-methoxy-4-oxo-4,9-dihydrothieno[2,3-b]quinoline-2-carbonitrile.

Example 11

Synthesis of 9-cyclopropyl-6-fluoro-3-hydroxyl-8-methoxy-7-(2-methylpyridin-4-yl-4-oxo-4,9-dihydrothieno[2,3-b]quinoline-2-carbonitrile

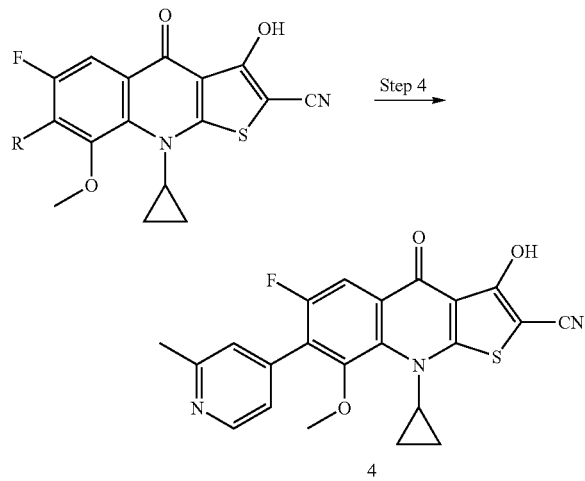

-continued

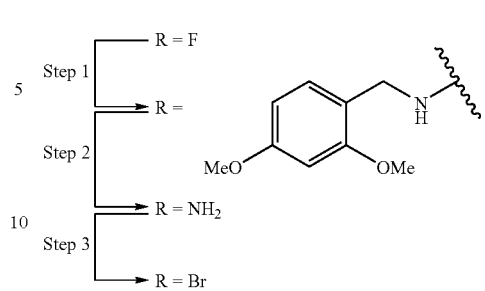

The starting material, 7-bromo-9-cyclopropyl-6-fluoro-3-hydroxyl-8-methoxy-4-oxo-4,9-dihydrothieno[2,3-b]quinoline-2-carbonitrile, is prepared using the 3-step fluoro-to-bromo conversion process depicted above. (See US 2008071086, and Hashimoto, et al., 2007) $^1$H NMR (DMF-$d_7$): δ 1.13-1.18 (m, 2H), 1.32-1.37 (m, 2H), 3.96 (s, 3H), 3.95-4.03 (m, 1H), 7.89 (d, J=8.0 Hz, 1H). $^{19}$F (DMF-$d_7$): δ −109.6 (s). LCMS: m/z calcd for $C_{16}H_{10}{}^{79}BrFN_2O_3S$ ([M]$^+$) 408. found ([M+H]$^+$) 409. The title compound is prepared from 2-methylpyridin-4-ylboronic acid and 7-bromo-9-cyclopropyl-6-fluoro-3-hydroxyl-8-methoxy-4-oxo-4,9-dihydrothieno[2,3-b]quinoline-2-carbonitrile using a procedure analogous to that describing the preparation of 9-cyclopropyl-6-fluoro-8-methoxy-7-(2-methylpyridin-4-yl)isothiazolo[5,4-b]quinoline-3,4(2H,9H)-dione. (See US 2008071086, and Hashimoto et al., 2007)

Example 12

Synthesis and Testing of Additional Compounds

The preparation of compounds listed in Table I can be carried out under conditions analogous to those described in the examples above.

Testing of select compounds is performed using the cytotoxicity assay described in Example 14.

TABLE I

| Cmp # | Structure | Name | Salt | MW | FW | MS | 1H NMR | 19F NMR | MSSA | MRSA |
|---|---|---|---|---|---|---|---|---|---|---|
| 5 | 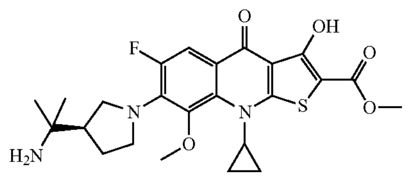 | (R)-methyl 7-(3-(2-aminopropan-2-yl)pyrrolidin-1-yl)-9-cyclopropyl-6-fluoro-3-hydroxyl-8-methoxy-4-oxo-4,9-dihydrothieno[2,3-b]quinoline-2-carboxylate | No salt | 489.6 | 489.6 | 490 (M + H) | 1.87-2.03 (m, 2H), 2.42 (m, 2H), 2.48 (s, 6H), 3.12 (m, 1H), 3.34 (m, 1H), 3.99 (m, 1H), 4.67 (s, 3H), 4.87-5.21 (m, 6H), 4.91 (s, 3H), 8.97 (d, J = 12.5 Hz, 1H), 12.38 (s, 2H) | −118.3 | 2 | 64 |
| 6 | 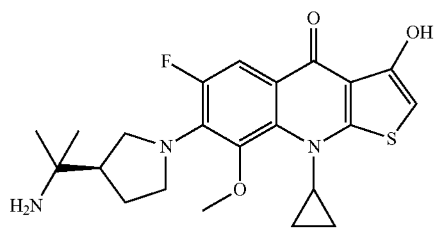 | (R)-7-(3-(2-aminopropan-2-yl)pyrrolidin-1-yl)-9-cyclopropyl-6-fluoro-3-hydroxyl-8-methoxythieno[2,3-b]quinolin-4(9H)-one | HCl | 431.5 | 468.0 | 432 | 0.91-0.98 (m, 2H), 1.15-1.32 (m, 2H), 1.33 (s, 6H), 1.83 (m, 1H), 2.02 (m, 1H), 3.41-3.78 (m, 5H), 3.57 (s, 3H), 3.65 (s, 1H), 3.89 (s, 2H), 7.46 (d, J = 12.5 Hz, 1H), 8.24 (bs, 2H) | −124.0 | 2 | 32 |
| 7 | 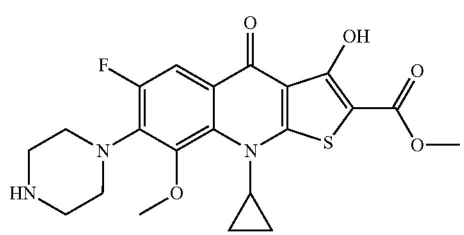 | methyl 9-cyclopropyl-6-fluoro-3-hydroxyl-8-methoxy-4-oxo-7-(piperazin-1-yl)-4,9-dihydrothieno[2,3-b]quinoline-2-carboxylate | No salt | 447.5 | 447.5 | 448 (M + H) | 0.84 (m, 2H), 1.20 (m, 2H), 2.89 (m, 2H), 3.15-3.48 (m, 7H), 3.65-3.83 (m, 7H), 6.53 (m, 1H), 7.63 (d, J = 12.5 Hz, 1H) | −124.7 | 3 | 32 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 8 | 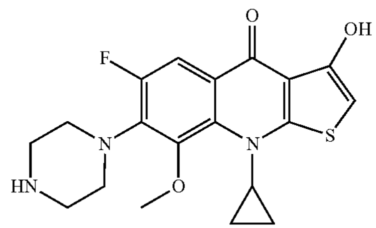 | 9-cyclopropyl-6-fluoro-3-hydroxyl-8-methoxy-7-(piperazin-1-yl)thieno[2,3-b]quinolin-4(9H)-one | HCl | 389.4 | 425.9 | 390 (M+H) | 0.97 (m, 2H), 1.20 (m, 2H), 3.17 (m, 4H), 3.50 (m, 4H), 3.65-3.83 (m, 3H), 3.75 (s, 3H), 7.54 (d, J = 12.5 Hz, 1H), 9.11 (s, 1H) | −123.4 | 32 | >64 |
| 9 | 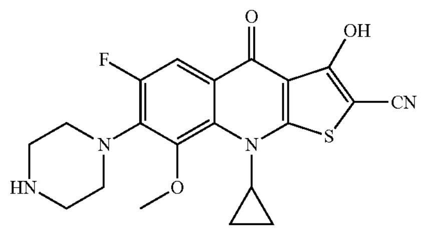 | 9-cyclopropyl-6-fluoro-3-hydroxyl-8-methoxy-4-oxo-7-(piperazin-1-yl)-4,9-dihydrothieno[2,3-b]quinoline-2-carbonitrile | HCl | 414.5 | 450.9 | 415 (M+H) | 0.97 (m, 2H), 1.17 (m, 2H), 3.05-3.60 (m, 4H), 3.78 (s, 3H), 7.54 (d, J = 12.5 Hz, 1H), 8.84 (s, 1H) | −124.0 | 0.06 | 0.75 |
| 10 | 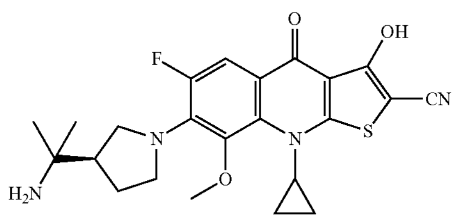 | (R)-7-(3-(2-aminopropan-2-yl)pyrrolidin-1-yl)-9-cyclopropyl-6-fluoro-3-hydroxy-8-methoxy-4-oxo-4,9-dihydrothieno[2,3-b]quinoline-2-carbonitrile | No salt | 456.5 | 456.5 | 457 (M+H) | 0.90 (m, 2H, c-Pr), 1.15 (m, 2H, c-Pr), 1.24 (s, 3H, methyl), 1.25 (s, 3H, methyl), 1.73 (m, 1H), 1.99 (m, 1H), 2.45 (m, 1H), 3.45 (s, 3H, methoxy), 3.15-3.87 (m, 5H), 7.51 (d, J$_{H-F}$ = 13.8 Hz, 1H), 7.92 (br, 2H) | −124.2 | 0.02 | 0.094 |

TABLE I-continued

| Cmp # | Structure | Name | Salt | MW | FW | MS | $^1$H NMR | $^{19}$F NMR | MSSA | MRSA |
|---|---|---|---|---|---|---|---|---|---|---|
| 11 | (structure) | 7-((R)-3-((S)-1-aminoethyl)pyrrolidin-1-yl)-9-cyclopropyl-6-fluoro-3-hydroxyl-8-methoxy-4-oxo-4,9-dihydrothieno[2,3-b]quinoline-2-carbonitrile | No salt | 442.5 | 442.5 | 443 (M+H) | 0.92 (m, 2H, c-Pr), 1.16 (m, 2H, c-Pr), 1.22 (d, 3H, J = 6.5 Hz), 1.68 (m, 1H), 2.02 (m, 1H), 2.29 (m, 1H), 3.45 (s, 3H, methoxy), 3.14-3.87 (m, 6H), 7.51 (d, $J_{H,F}$ = 13.7 Hz, 1H), 7.87 (br, 2H) | −124.3 | 0.02 | 0.094 |
| 12 | (structure) | 9-cyclopropyl-6-fluoro-3-hydroxyl-8-methoxy-7-(piperazin-1-yl)-2-pivaloylthieno[2,3-b]quinolin 4(9H)-one | HCl | 473.6 | 510.0 | 474 (M+H) | 0.87 (m, 2H), 1.17 (m, 2H), 1.26 (s, 9H), 3.18 (m, 4H), 3.49 (m, 4H), 3.49 (s, 3H), 3.64 (m, 1H) 7.62 (d, J = 12.5 Hz, 1H), 9.14, (bs, 1H), 12.66 (bs, 1H) | −124.0 | 8 | 8 |
| 13 | (structure) | (R)-7-(3-(2-aminopropan-2-yl)pyrrolidin-1-yl)-9-cyclopropyl-6-fluoro-3-hydroxyl-8-methoxy-2-nitrothieno[2,3-b]quinolin-4(9H)-one | No salt | 476.5 | 476.5 | 477 (M+H) | 1.00 (m, 2H, c-Pr), 1.13 (m, 2H, c-Pr), 1.30 (s, 3H, methyl) 1.33 (s, 3H, methyl), 1.77 (m, 1H), 2.03 (m, 1H), 2.48 (m, 1H), 3.46 (s, 3H, methoxy), 3.44-3.91 (m, 5H), 7.45 (d, $J_{H,F}$ = 13.8 Hz, 1H), 8.06 (br, 2H) | −124.1 | 8 | 32 |

TABLE I-continued

| Cmp # | Structure / Name | Salt | MW | FW | MS | ¹H NMR | ¹⁹F NMR | MSSA | MRSA |
|---|---|---|---|---|---|---|---|---|---|
| 14 | 9-cyclopropyl-6-fluoro-3-hydroxyl-8-methoxy-2-(phenylsulfonyl)-7-(piperazin-1-yl)thieno[2,3-b]quinolin-4(9H)-one | HCl | 529.6 | 566.1 | 530 (M + H) | 0.89 (m, 2H), 1.15 (m, 2H), 3.00-3.90 (m, 3H), 7.63 (m, 9H), 3.37 (s, 5H), 7.82 (d, J = 12.5 Hz, 1H), 9.07, (bs, 1H) | −124.6 | 1 | 16 |
| 15 | 9-cyclopropyl-2-(3,4-difluorophenyl)-6-fluoro-3-hydroxyl-8-methoxy-7-(piperazin-1-yl)thieno[2,3-b]quinolin-4(9H)-one | HCl | 501.5 | 538.0 | 502 (M + H) | 0.89 (m, 2H), 1.17 (m, 2H), 3.20 (m, 4H), 3.26 (s, 3H), 3.49 (m, 4H), 3.84 (m, 1H), 7.44 (m, 2H), 7.61 (d, J = 12.5 Hz, 1H), 7.70 (m, 1H), 9.02, (bs, 1H), 10.49 (m, 1H) | −124.2 (s), −137.8 (d), −141.4 (d) J = 22.5 Hz | 8 | 4 |
| 16 | 9-cyclopropyl-8-(difluoromethoxy)-3-hydroxyl-4-oxo-7-(piperazin-1-yl)-4,9-dihydrothieno[2,3-b]quinoline-2-carbonitrile | HCl | 432.4 | 468.9 | 433 (M + H) | TFA-d: 1.08 (m, 2H), 1.52 (m, 2H), 3.53-3.74 (m, 8H), 3.99 (s, 1H), 4.07 (m, 1H), 6.34 (t, J = 72.3 Hz, 1H), 7.30 (d, J = 8.7 Hz, 1H), 8.34 (d, J = 9.3 Hz, 1H) | −81.9 | 4 | 64 |
| 17 | 9-cyclopropyl-8-(difluoromethoxy)-7-(dimethylamino)-3-hydroxyl-4-oxo-4,9-dihydrothieno[2,3-b]quinoline-2-carbonitrile | HCl | 391.4 | 427.9 | 392 (M + H) | 0.97-1.02 (m, 2H), 1.23-1.29 (m, 2H), 3.02 (s, 6H), 3.74 (m, 1H), 6.72 (t, J = 75.0 Hz, 1H), 7.16 (d, J = 9.0 Hz, 1H), 7.99 (d, J = 9.0 Hz, 1H) | −82.9 | 4 | 64 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 3 | 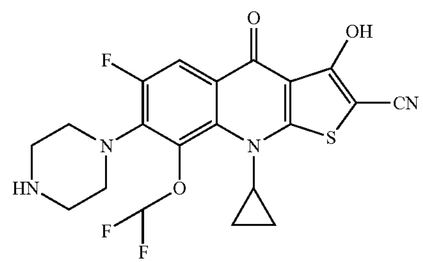 | 9-cyclopropyl-8-(difluoromethoxy)-6-fluoro-3-hydroxyl-4-oxo-7-(piperazin-1-yl)-4,9-dihydrothieno[2,3-b]quinoline-2-carbonitrile | HCl | 450.4 | 486.9 | 451 (M+H) | 1.02 (m, 2H), 1.27 (m, 2H), 2.73 (m, 4H), 3.35 (m, 4H), 3.76 (m, 1H), 7.01 (t, J = 74.1 Hz, 1H), 7.87 (d, J = 11.7 Hz, 1H), 9.038 (brs, 1H) | −83.2 (2F), −123.9 (1F) | 0.25 | 4 |
| 18 | 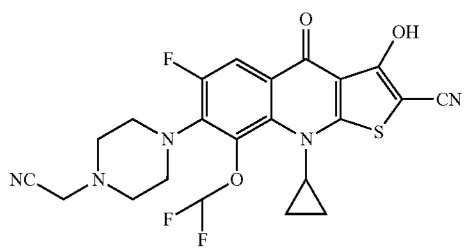 | 7-(4-(cyanomethyl)piperazin-1-yl)-9-cyclopropyl-8-(difluoromethoxy)-6-fluoro-3-hydroxyl-4-oxo-4,9-dihydrothieno[2,3-b]quinoline-2-carbonitrile | HCl | 489.5 | 525.9 | 490 (M+H) | TFA-d: 1.07 (m, 2H), 1.47 (m, 2H), 3.68 (m, 9H), 4.28 (m, 1H), 4.61 (s, 2H), 6.46 (t, J = 72.0 Hz, 2H), 8.06 (d, J = 11.7 Hz, 1H) | −83.3 (2F), −123.6 (1F) | 0.13 | 4 |
| 19 | 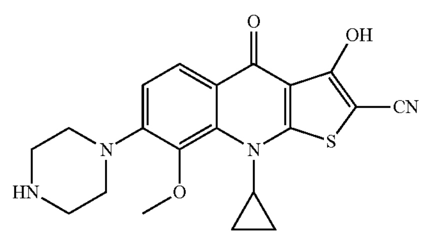 | 9-cyclopropyl-3-hydroxyl-8-methoxy-4-oxo-7-(piperazin-1-yl)-4,9-dihydrothieno[2,3-b]quinoline-2-carbonitrile | TFA | 396.5 | 510.5 | 397 (M+H) | CD₃OD: 0.89 (br, 2H), 1.24 (m, 2H), 3.37 (m, 4H), 3.53 (m, 4H), 3.71 (s, 3H), 3.81 (m, 1H), 7.12 (d, J = 8.67 Hz, 1H), 7.95 (d, J = 8.67 Hz, 1H) | N/A | 0.25 | 4 |
| 20 | 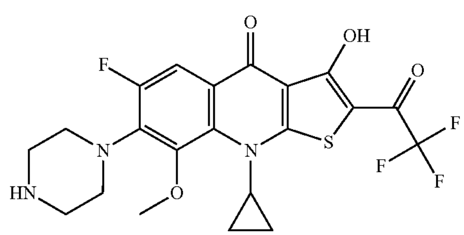 | 9-cyclopropyl-6-fluoro-3-hydroxyl-8-methoxy-7-(piperazin-1-yl)-2-(2,2,2-trifluoroacetyl)thieno[2,3-b]quinolin-4(9H)-one | HCl | 485.5 | 521.9 | 486 (M+H) | 1.05 (m, 2H), 1.31 (m, 2H), 3.32 (m, 4H), 3.62 (m, 4H), 3.81 (s, 3H), 3.96 (m, 1H), 7.77 (d, J = 12.5 Hz, 1H), 9.17 (bs, 1H) | −74.0 (3F), −123.2 (1F) | 64 | >64 |

TABLE I-continued

| Cmp # | Structure | Name | Salt | MW | FW | MS | $^1$H NMR | $^{19}$F NMR | MSSA | MRSA |
|---|---|---|---|---|---|---|---|---|---|---|
| 2 | 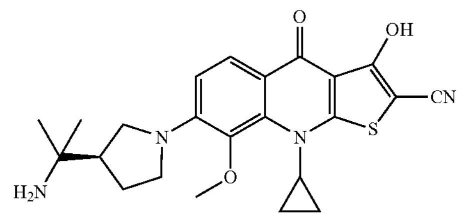 | (R)-7-(3-(2-aminopropan-2-yl)pyrrolidin-1-yl)-9-cyclopropyl-3-hydroxyl-8-methoxy-4-oxo-4,9-dihydrothieno[2,3-b]quinoline-2-carbonitrile | TFA | 438.5 | 552.6 | 439 (M + H) | Acetic acid-d$_4$: 0.93 (br, 2H), 1.21 (br, 2H), 1.41 (s, 6H), 2.12 (br, 1H), 2.64 (m, 2H), 3.44 (s, 3H), 3.55 (m, 5H), 6.85 (d, J = 8.85 Hz, 1H), 7.89 (d, J = 8.85 Hz, 1H) | N/A | 0.06 | 0.42 |
| 21 | 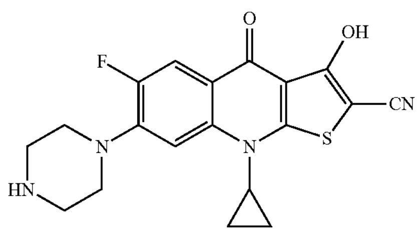 | 9-cyclopropyl-6-fluoro-3-hydroxyl-4-oxo-7-(piperazin-1-yl)-4,9-dihydrothieno[2,3-b]quinoline-2-carbonitrile | No salt | 384.4 | 384.4 | 385 (M + H) | Acetic acid-d$_4$: 1.42 (br, 2H), 1.59 (br, 2H), 3.68 (m, 9H), 7.58 (d, J = 6.59 Hz, 1H), 7.82 (d, J = 12.81 Hz, 1H) | −124.8 | 0.13 | 2 |
| 22 | 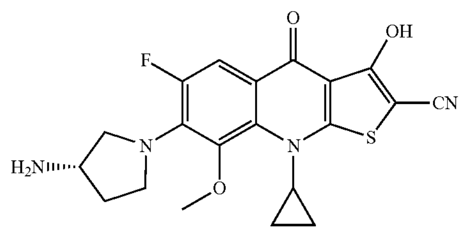 | (S)-7-(3-aminopyrrolidin-1-yl)-9-cyclopropyl-6-fluoro-3-hydroxyl-8-methoxy-4-oxo-4,9-dihydrothieno[2,3-b]quinoline-2-carbonitrile | HCl | 414.5 | 450.9 | 415 (M + H) | 0.89-0.90 (m, 2H), 1.12-1.15 (m, 2H), 1.84-2.02 (m, 1H), 2.19-2.25 (m, 1H), 3.41 (s, 3H), 3.48-3.81 (m, 6H), 7.53 (d, J = 15.0 Hz, 1H), 8.28 (brs, 3H), | −124.5 | 0.03 | 0.25 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 23 | 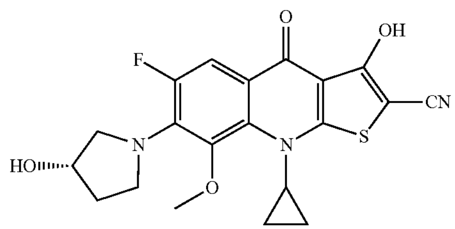 | (S)-9-cyclopropyl-6-fluoro-3-hydroxyl-7-(3-hydroxyl-pyrrolidin-1-yl)-8-methoxy-4-oxo-4,9-dihydrothieno[2,3-b]quinoline-2-carbonitrile | No salt | 415.4 | 415.4 | 416 (M+H) | 0.96 (m, 2H), 1.18-1.24 (m, 2H), 1.89-1.99 (m, 2H), 3.31 (d, J = 12.0 Hz, 1H), 3.49 (s, 3H), 3.53-3.57 (m, 1H), 3.80-4.15 (m, 4H), 4.57 (brs, 1H), 7.54 (d, J = 14.1 Hz, 1H). | −124.9 | 0.03 | 0.5 |
| 24 | 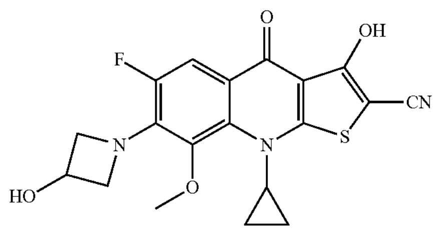 | 9-cyclopropyl-6-fluoro-3-hydroxyl-7-(3-hydroxylazetidin-1-yl)-8-methoxy-4-oxo-4,9-dihydrothieno[2,3-b]quinoline-2-carbonitrile | No salt | 401.4 | 401.4 | 402 (M+H) | 0.92-0.96 (m, 2H), 1.16-1.21 (m, 2H), 3.53 (s, 3H), 3.76-3.81 (m, 1H), 4.01-4.07 (m, 2H), 4.51-4.54 (m, 3H), 7.53 (d, J = 12.0 Hz, 1H). | −132.5 | 0.06 | 1 |
| 25 | 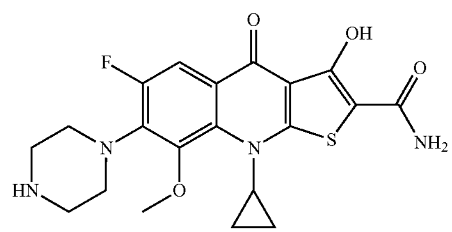 | 9-cyclopropyl-6-fluoro-3-hydroxyl-8-methoxy-4-oxo-7-(piperazin-1-yl)-4,9-dihydrothieno[2,3-b]quinoline-2-carboxamide | HCl | 432.5 | 468.9 | 433 (M+H) | 0.89-0.92 (m, 2H), 1.19-1.26 (m, 2H), 3.17 (brs, 4H), 3.55 (brs, 4H), 3.73 (s, 3H), 3.81-3.87 (m, 1H), 7.68 (d, J = 12.0 Hz, 1H), 9.18 (brs, 2H). | −124.6 | 0.25 | 2 |
| 26 | 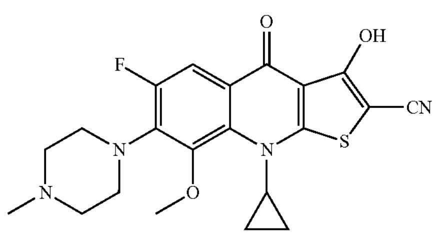 | 9-cyclopropyl-6-fluoro-3-hydroxyl-8-methoxy-7-(4-methylpiperazin-1-yl)-4-oxo-4,9-dihydrothieno[2,3-b]quinoline-2-carbonitrile | HCl | 428.5 | 464.9 | 429 (M+H) | 0.97 (m, 2H), 1.19-1.23 (m, 2H), 2.88 (s, 3H), 3.32 (brs, 4H), 3.59 (brs, 4H), 3.74 (s, 3H), 3.82-3.88 (m, 1H), 7.69 (d, J = 12.0 Hz, 1H). | −124.0 | 0.13 | 1 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 4 | 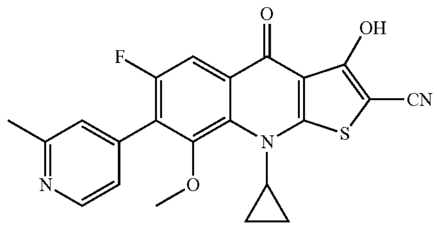 | 9-cyclopropyl-6-fluoro-3-hydroxyl-8-methoxy-7-(2-methylpyridin-4-yl)-4-oxo-4,9-dihydrothieno[2,3-b]quinoline-2-carbonitrile | HCl | 421.4 | 457.9 | 422 (M+H) | TFA-d: 8.73 (d, J = 6.3 Hz, 1H), 8.08-8.15 (m, 3H), 3.93-3.99 (m, 1H),3.54 (, 3H), 2.93 (s, 3H), 1.46-1.58 (m, 2H), 1.15-1.18 (m, 2H). | −117.7 | 0.02 | 0.13 |
| 27 | 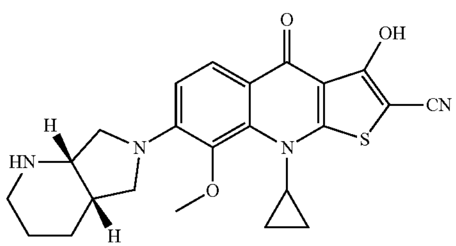 | 9-cyclopropyl-3-hydroxyl-8-methoxy-4-oxo-7-((4aS,7aS)-tetrahydro-1H-pyrrolo[3,4-b]pyridin-6(2H,7H,7aH)-yl)-4,9-dihydrothieno[2,3-b]quinoline-2-carbonitrile | TFA | 436.5 | 550.6 | 437 (M+H) | 0.96 (m, 2H), 1.22 (br, 2H), 1.81 (m, 4H), 2.87 (m, 2H), 3.24 (m, 3H), 3.58 (m, 1H), 3.88 (m, 1H), 3.93 (m, 2H), 6.94 (d, J = 8.85 Hz, 1H), 7.87 (d, J = 8.85 Hz, 1H) | N/A | 0.5 | 8 |
| 28 | 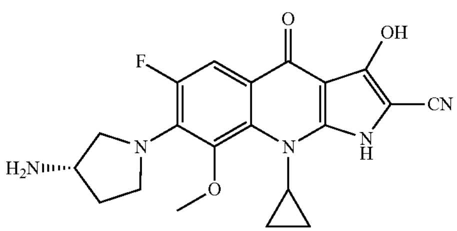 | (S)-7-(3-aminopyrrolidin-1-yl)-9-cyclopropyl-6-fluoro-3-hydroxyl-8-methoxy-4-oxo-4,9-dihydro-1H-pyrrolo[2,3-b]quinoline-2-carbonitrile | HCl | 397.4 | 433.9 | 398 (M+H) | CD₃OD: 0.84 (m, 2H), 1.31 (m, 2H), 2.14 (m, 1H), 2.52 (s, 3H), 3.62-4.08 (m, 6H), 7.82 (d, J = 14.4 Hz, 1H). | −125.7 | 64 | ND |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 29 | 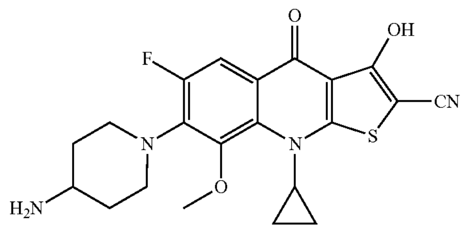 | 7-(4-aminopiperidin-1-yl)-9-cyclopropyl-6-fluoro-3-hydroxyl-8-methoxy-4-oxo-4,9-dihydrothieno[2,3-b]quinoline-2-carbonitrile | HCl | 428.5 | 464.9 | 429 (M+H) | 0.95 (m, 2H), 1.21-1.28 (m, 2H), 1.71-1.79 (m, 2H), 2.00-2.27 (m, 2H), 2.93-2.99 (m, 2H), 3.23 (m, 1H), 3.50-3.55 (m, 2H), 3.69 (s, 3H), 3.82-3.85 (m, 1H), 7.65 (d, J = 12.0 Hz, 1H), 8.06 (brs, 1H). | −123.9 | 0.03 | 0.5 |
| 30 | 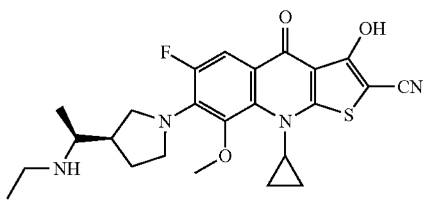 | 9-cyclopropyl-7-((R)-3-((S)-1-(ethylamino)ethyl)pyrrolidin-1-yl)-6-fluoro-3-hydroxyl-8-methoxy-4-oxo-4,9-dihydrothieno[2,3-b]quinoline-2-carbonitrile | HCl | 470.6 | 507.0 | 471 (M+H) | 0.96 (m, 2H, c-Pr), 1.22 (m, 2H, c-Pr), 1.25 (t, 3H, J = 7.1 Hz), 1.31 (d, 3H, J = 6.6 Hz), 1.79 (m, 1H), 2.10 (m, 1H), 2.64 (m, 1H), 3.00 (m, 2H, J = 7.1 Hz), 3.35 (m, 1H), 3.51 (s, 3H, methoxy), 3.56 (m, 2H), 3.66-3.86 (m, 3H), 7.52 (d, $J_{H-F}$ = 13.8 Hz, 1H), 8.85 (br, 1H), 9.15 (br, 1H) | −124.3 | 0.03 | 0.13 |

TABLE I-continued

| Cmp # | Structure | Name | Salt | MW | FW | MS | 1H NMR | 19F NMR | MSSA | MRSA |
|---|---|---|---|---|---|---|---|---|---|---|
| 31 | 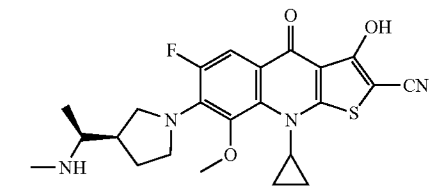 | 9-cyclopropyl-6-fluoro-3-hydroxyl-8-methoxy-7-((R)-3-((S)-1-(methylamino)ethyl)pyrrolidin-1-yl)-4-oxo-4,9-dihydrothieno[2,3-b]quinoline-2-carbonitrile | HCl | 456.5 | 493.0 | 457 (M + H) | 0.94 (m, 2H, c-Pr), 1.22 (m, 2H, c-Pr), 1.29 (d, 3H, J = 6.5 Hz), 1.75 (m, 1H), 2.10 (m, 1H), 2.54 (s, 3H, —NMe), 2.72 (m, 1H), 3.31 (m, 1H), 3.51 (s, 3H, methoxy), 3.55 (m, 2H), 3.66-3.77 (m, 3H), 7.55 (d, $J_{HF}$ = 13.8 Hz, 1H), 8.96 (br, 1H), 9.17 (br, 1H) | −124.4 | 0.03 | 0.25 |
| 32 | 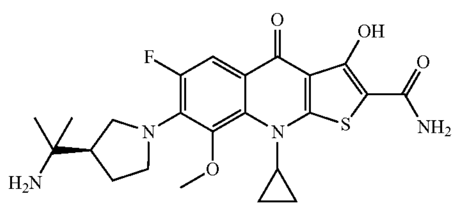 | (R)-7-(3-(2-aminopropan-2-yl)pyrrolidin-1-yl)-9-cyclopropyl-6-fluoro-3-hydroxyl-8-methoxy-4-oxo-4,9-dihydrothieno[2,3-b]quinoline-2-carboxamide | HCl | 474.5 | 511.0 | 475 (M + H) | 0.90-0.91 (m, 2H), 1.15-1.25 (m, 2H), 1.33 (d, J = 2.7 Hz, 6H), 1.75-1.88 (m, 1H), 2.06 (m, 1H), 3.52 (s, 3H), 3.52-3.84 (m, 6H), 7.57 (d, J = 13.8 Hz, 1H), 8.24 (brs, 2H). | −124.6 | 0.13 | 0.5 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 33 | 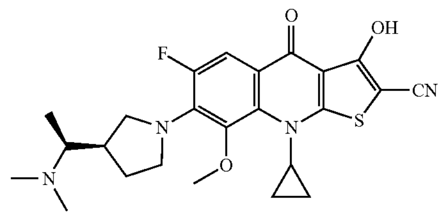 | 9-cyclopropyl-7-((R)-3-((S)-1-(dimethylamino)ethyl)pyrrolidin-1-yl)-6-fluoro-3-hydroxyl-8-methoxy-4-oxo-4,9-dihydrothieno[2,3-b]quinoline-2-carbonitrile | HCl | 470.6 | 507.0 | 471 (M+H) | 0.94 (m, 2H, c-Pr), 1.22 (m, 2H, c-Pr), 1.31 (d, 3H, J = 6.6 Hz), 1.72 (m, 1H), 2.10 (m, 1H), 2.60 (m, 1H), 2.68 (d, 3H, J = 4.6 Hz), 2.75 (d, 3H, J = 4.6 Hz), 3.51 (s, 3H, methoxy), 3.43-3.67 (m, 3H), 3.80 (m, 3H), 5.30-6.40 (br, 1H), 7.54 (d, $J_{HF}$ = 13.7 Hz, 1H), 10.39 (brs, 1H) | −124.4 | 0.06 | 0.5 |
| 1 | 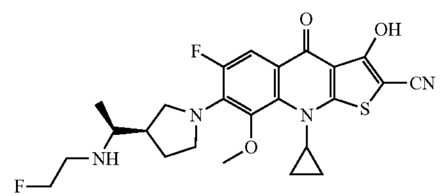 | 9-cyclopropyl-6-fluoro-7-((R)-3-((S)-1-(2-fluoroethylamino)ethyl)pyrrolidin-1-yl)-3-hydroxyl-8-methoxy-4-oxo-4,9-dihydrothieno[2,3-b]quinoline-2-carbonitrile | HCl | 488.6 | 525.0 | 489 (M+H) | 0.95 (m, 2H, c-Pr), 1.15-1.33 (m, 2H, c-Pr), 1.34 (d, 3H, J = 6.2 Hz), 1.79 (m, 1H), 2.10 (m, 1H), 2.64 (m, 1H), 3.51 (s, 3H, methoxy), 3.22-3.55 (m, 5H), 3.66-3.87 (m, 3H), 4.75 (t, 1H, J = 4.6 Hz), 4.90 (t, 1H, J = 4.6 Hz), 7.53 (d, $J_{HF}$ = 13.8 Hz, 1H), 9.32 (brs, 1H), 9.52 (brs, 1H) | −124.4 | 0.02 | 0.13 |

TABLE I-continued

| Cmp # | Structure | Name | Salt | MW | FW | MS | $^1$H NMR | $^{19}$F NMR | MSSA | MRSA |
|---|---|---|---|---|---|---|---|---|---|---|
| 34 | 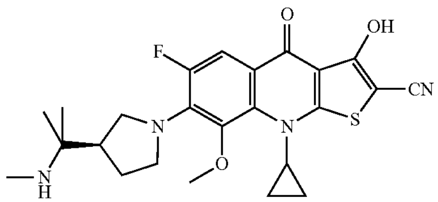 | (R)-9-cyclopropyl-6-fluoro-3-hydroxyl-8-methoxy-7-(3-(2-(methylamino)propan-2-yl)pyrrolidin-1-yl)-4-oxo-4,9-dihydrothieno[2,3-b]quinoline-2-carbonitrile | HCl | 470.6 | 507.0 | 471 (M+H) | 0.94 (m, 2H, c-Pr), 1.22 (m, 2H, c-Pr), 1.30 (s, 3H), 1.32 (s, 3H), 1.81 (m, 1H), 2.05 (m, 1H), 2.50 (s, 3H, N-methyl), 2.65 (m, 1H), 3.52 (s, 3H, methoxy), 3.55-3.87 (m, 5H), 7.53 (d, $J_{H,F}$ = 13.7 Hz, 1H), 9.18 (brs, 2H) | −124.2 | 0.06 | 0.5 |
| 35 | 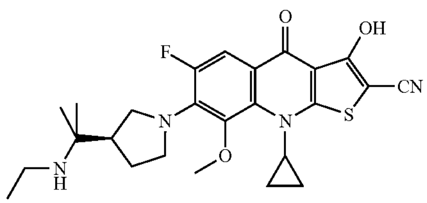 | (R)-9-cyclopropyl-7-(3-(2-(ethylamino)propan-2-yl)pyrrolidin-1-yl)-6-fluoro-3-hydroxyl-8-methoxy-4-oxo-4,9-dihydrothieno[2,3-b]quinoline-2-carbonitrile | HCl | 484.6 | 521.1 | 485 (M+H) | 0.96 (m, 2H, c-Pr), 1.34 (s, 3H), 1.37 (s, 3H), 1.15-1.52 (m, 5H), 1.82 (m, 1H), 2.07 (m, 1H), 2.67 (m, 1H), 3.00 (m, 2H), 3.52 (s, 3H, methoxy), 3.50-3.89 (m, 5H), 7.53 (d, $J_{H,F}$ = 13.7 Hz, 1H), 8.31 (brs, 1H), 8.90 (brs, 1H) | −124.2 | 0.06 | 0.5 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 36 | 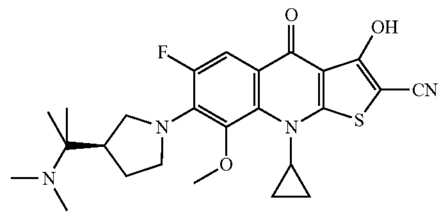 | (R)-9-cyclopropyl-7-(3-(2-(dimethylamino)propan-2-yl)pyrrolidin-1-yl)-6-fluoro-3-hydroxyl-8-methoxy-4-oxo-4,9-dihydrothieno[2,3-b]quinoline-2-carbonitrile | HCl | 484.6 | 521.1 | 485 (M+H) | 0.95 (m, 2H, c-Pr), 1.22 (m, 2H, c-Pr), 1.35 (s, 3H), 1.39 (s, 3H), 1.84 (m, 1H), 2.14 (m, 1H), 2.69 (m, 1H), 2.71 (s, 6H, N,N-dimethyl), 3.53 (s, 3H, methoxy), 3.48-3.88 (m, 5H), 7.51 (d, $J_{H-F}$ = 13.8 Hz, 1H), 10.57 (brs, 1H) | −124.2 | 0.25 | 2 |
| 37 | 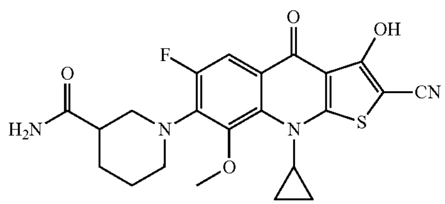 | 1-(2-cyano-9-cyclopropyl-6-fluoro-3-hydroxyl-8-methoxy-4-oxo-4,9-dihydrothieno[2,3-b]quinolin-7-yl)piperidine-3-carboxamide | HCl | 456.5 | 493.0 | 457 (M+H) | 0.95 (m, 2H), 1.23 (m, 2H), 1.59-1.76 (m, 3H), 1.93-1.95 (m, 1H), 3.10-3.26 (m, 3H), 3.36-3.46 (m, 2H), 3.68 (s, 3H), 3.82-3.87 (m, 1H), 6.85 (brs, 1H), 7.36 (brs, 1H), 7.63 (d, J = 12.0 Hz, 1H) | −123.7 | 0.03 | 0.25 |
| 38 | 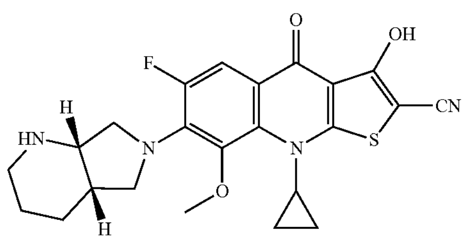 | 9-cyclopropyl-6-fluoro-3-hydroxyl-8-methoxy-4-oxo-7-((4aS,7aS)-tetrahydro-1H-pyrrolo[3,4-b]pyridin-6(2H,7H,7aH)-yl)-4,9-dihydrothieno[2,3-b]quinoline-2-carbonitrile | No salt | 454.5 | 454.5 | 455 (M+H) | 0.94 (m, 2H), 1.24 (m, 2H, c-Pr), 1.78 (m, 5H), 2.65 (m, 1H), 2.75-3.06 (m, 3H), 3.15-3.47 (m, 3H), 3.52 (s, 3H, methoxy), 3.71 (m, 2H), 7.57 (d, $J_{H-F}$ = 14.2 Hz, 1H), 9.19 (brs, 1H) | −124.2 | 0.5 | 8 |

| Cmp # | Structure | Name | Salt | MW | FW | MS | ¹H NMR | ¹⁹F NMR | MSSA | MRSA |
|---|---|---|---|---|---|---|---|---|---|---|
| 39 | 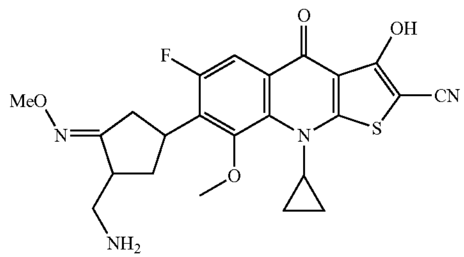 | (Z)-7-(3-(aminomethyl)-4-(methoxyimino)pyrrolidin-1-yl)-9-cyclopropyl-6-fluoro-3-hydroxyl-8-methoxy-4-oxo-4,9-dihydrothieno[2,3-b]quinoline-2-carbonitrile | No salt | 471.5 | 471.5 | 472 (M+H) | 0.96 (m, 2H, c-Pr), 1.23 (m, 2H, c-Pr), 2.41 (m, 2H), 3.13 (m, 1H), 3.26 (m, 1H), 3.47 (m, 1H), 3.51 (s, 3H, methoxy), 3.65 (m, 2H), 3.89 (s, 3H, N-methoxy), 4.01 (m, 2H), 7.64 (d, $J_{H-F}$=13.2 Hz, 1H), 7.93 (brs, 1H) | −124.0 | 0.13 | 1 |
| 40 | 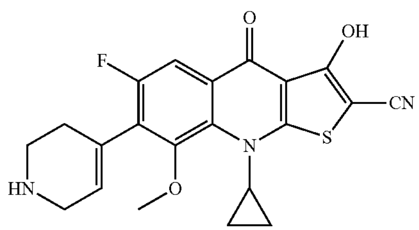 | 9-cyclopropyl-6-fluoro-3-hydroxyl-8-methoxy-4-oxo-7-(1,2,3,6-tetrahydropyridin-4-yl)-4,9-dihydrothieno[2,3-b]quinoline-2-carbonitrile | HCl | 411.4 | 447.9 | 412 (M+H) | 0.93-0.98 (m, 2H), 1.17-1.27 (m, 2H), 2.32-2.63 (m, 2H), 3.22-3.34 (m, 2H), 3.49-3.90 (m, 3H), 3.67 (s, 3H), 5.82 (brs, 0.2H), 5.97 (brs, 0.8H), 7.73 (d, J = 9.3 Hz, 1H) | −117.3 | 0.5 | 4 |
| 41 | 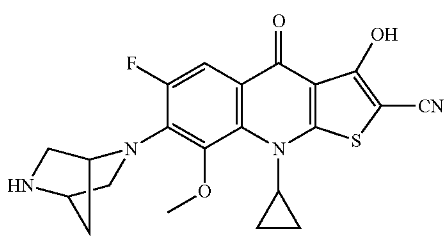 | 7-(2,5-diazabicyclo[2.2.1]heptan-2-yl)-9-cyclopropyl-6-fluoro-3-hydroxyl-8-methoxy-4-oxo-4,9-dihydrothieno[2,3-b]quinoline-2-carbonitrile | 2HCl | 426.5 | 499.4 | 427 (M+H) | 0.95 (m, 2H, c-Pr), 1.23 (m, 3H), 1.99 (m, 1H), 2.13 (m, 1H), 3.52 (s, 3H, methoxy), 3.70-4.02 (m, 6H), 7.63 (d, $J_{H-F}$=14.0 Hz, 1H), 9.17 (br, 1H), 9.60 (br, 1H) | −126.1 | 0.13 | 1 |

TABLE I-continued

| Cmp # | Structure / Name | Salt | MW | FW | MS | ¹H NMR | ¹⁹F NMR | MSSA | MRSA |
|---|---|---|---|---|---|---|---|---|---|
| 42 | 9-cyclopropyl-6-fluoro-7-((3aR,6aS)-hexahydropyrrolo[3,4-c]pyrrol-2(1H)-yl)-3-hydroxyl-8-methoxy-4-oxo-4,9-dihydrothieno[2,3-b]quinoline-2-carbonitrile | 2HCl | 440.5 | 513.4 | 441 (M+H) | 0.94 (m, 2H, c-Pr), 1.20 (m, 2H, c-Pr), 3.02 (m, 4H), 3.26 (m, 1H), 3.44-3.65 (m, 5H), 3.50 (s, 3H, methoxy), 3.71 (m, 1H), 7.58 (d, $J_{HF}$ = 13.3 Hz, 1H), 9.41 (br, 1H), 9.59 (br, 1H) | -123.7 | 0.25 | 1 |
| 43 | 9-cyclopropyl-6-fluoro-8-methoxy-3,4-dioxo-7-(4-(trifluoromethyl)piperidin-1-yl)-2,3,4,9-tetrahydrothieno[2,3-b]quinoline-2-carbonitrile | No salt | 481.5 | 481.5 | 482 (M+H) | 0.88-0.95 (4H, m), 1.26-1.32 (2H, m), 1.72-1.88 (2H, m), 2.00 (2H, d, J = 11.8 Hz), 3.23 (2H, t, J = 12.4 Hz), 3.64-3.72 (3H, m), 3.72 (3H, s), 7.79 (1H, d, J = 11.9 Hz) | -122.4 (1F), -73.9 (3F) | 1 | 8 |
| 44 | 7-((R)-3-(1H-1,2,4-triazol-5-yl)pyrrolidin-1-yl)-9-cyclopropyl-6-fluoro-8-methoxy-3,4-dioxo-2,3,4,9-tetrahydrothieno[2,3-b]quinoline-2-carbonitrile | HCl | 466.5 | 502.9 | 467 (M+H) | 0.96 (m, 2H), 1.21 (m, 2H), 2.29 (m, 1H), 2.38 (m, 1H), 3.47 (s, 3H), 3.64-3.84 (m, 4H), 3.93 (m, 2H), 7.54 (d, $J_{HF}$ = 14.0 Hz, 1H), 8.61 (s, 1H) | -124.8 | 0.02 | 0.13 |

TABLE I-continued

| Cmp # | Structure / Name | Salt | MW | FW | MS | ¹H NMR | ¹⁹F NMR | MSSA | MRSA |
|---|---|---|---|---|---|---|---|---|---|
| 45 | 1-(2-cyano-9-cyclopropyl-6-fluoro-8-methoxy-3,4-dioxo-2,3,4,9-tetrahydrothieno[2,3-b]quinolin-7-yl)piperidine-4-carboxamide | No salt | 456.5 | 456.5 | 457 (M+H) | 0.91-0.97 (2H, m), 1.18-1.26 (2H, m), 1.71-1.83 (4H, m), 2.27-2.34 (1H, m), 3.16 (2H, t, J = 11.6 Hz), 3.51 (2H, d, J = 13.0 Hz), 3.68 (3H, s), 3.82-3.87 (1H, m), 6.80 (1H, brs), 7.30 (1H, brs), 7.63 (1H, d, J = 12.2 Hz) | -123.3 | 0.03 | 0.5 |
| 46 | (2S)-1-(2-cyano-9-cyclopropyl-6-fluoro-8-methoxy-3,4-dioxo-2,3,4,9-tetrahydrothieno[2,3-b]quinolin-7-yl)pyrrolidine-2-carboxamide | HCl | 442.5 | 478.9 | 443 (M+H) | 0.91-0.93 (2H, m), 1.16-1.23 (2H, m), 1.78-1.80 (1H, m), 2.02 (1H, m), 2.32-2.44 (1H, m), 3.45-3.47 (1H, m), 3.58 (3H, s), 3.78-3.92 (3H, m), 4.67-4.69 (1H, m), 6.92 (1H, brs), 7.38 (1H, brs), 7.52 (1H, d, J = 13.9 Hz) | -123.6 | 4 | 64 |
| 47 | (1S)-5-fluoro-1-methyl-7,8-dioxo-4-(piperazin-1-yl)-2,7,8,9-tetrahydro-1H-[1,4]oxazino[2,3,4-ij]thieno[2,3-b]quinoline-9-carbonitrile | HCl | 400.4 | 436.9 | 401 (M+H) | TFA-d: 1.70 (3H, d, J = 6.6 Hz), 3.68-4.01 (9H, m), 4.48 (1H, d, J = 11.8 Hz), 4.72-4.79 (2H, m), 7.88-7.95 (1H, m) | CD₃OD: -125.2 | 1 | 4 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 48 | 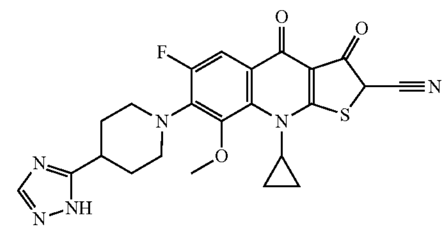 | 7-(4-(1H-1,2,4-triazol-5-yl)piperidin-1-yl)-9-cyclopropyl-6-fluoro-8-methoxy-3,4-dioxo-2,3,4,9-tetrahydrothieno[2,3-b]quinoline-2-carbonitrile | HCl | 480.5 | 517.0 | 481 (M+H) | 0.95 (m, 2H), 1.22 (m, 2H), 1.93 (m, 2H), 2.11 (m, 2H), 3.32 (m, 2H), 3.17 (m, 1H), 3.56 (m, 2H), 3.71 (s, 3H), 3.84 (m, 1H), 7.63 (d, $J_{HF}$ = 12.0 Hz, 1H), 8.82 (s, 1H) | −123.7 | 0.03 | 0.25 |
| 49 | 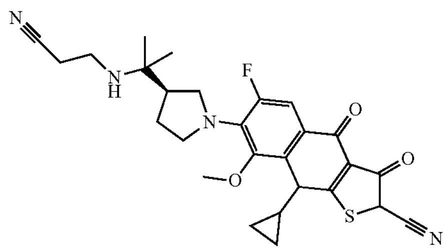 | 7-((R)-3-(2-(2-cyanoethylamino)propan-2-yl)pyrrolidin-1-yl)-9-cyclopropyl-6-fluoro-8-methoxy-3,4-dioxo-2,3,4,9-tetrahydrothieno[2,3-b]quinoline-2-carbonitrile | HCl | 509.6 | 582.5 | 510 (M+H) | 0.94 (m, 2H), 1.22 (m, 2H), 1.36 (s, 3H), 1.38 (s, 3H), 1.81 (m, 1H), 2.09 (m, 1H), 2.65 (m, 1H), 3.08 (t, J = 7.5 Hz, 2H), 3.34 (m, 2H), 3.52 (s, 3H), 3.50-3.86 (m, 5H), 7.55 (d, $J_{HF}$ = 3.5 Hz, 1H), 9.37 (br, 1H) | −124.2 | 0.06 | 0.5 |
| 50 | 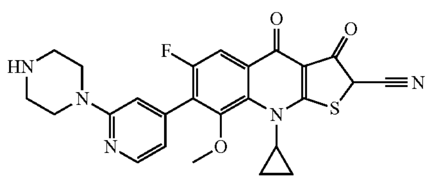 | 9-cyclopropyl-6-fluoro-8-methoxy-3,4-dioxo-7-(2-(piperazin-1-yl)pyridin-4-yl)-2,3,4,9-tetrahydrothieno[2,3-b]quinoline-2-carbonitrile | HCl | 491.5 | 528.0 | 492 (M+H) | 1.06-1.07 (2H, m), 1.25-1.28 (2H, m), 2.21 (4H, m), 3.50 (3H, s), 3.79-3.89 (5H, m), 6.89 (1H, d, 5.0 Hz), 7.09 (1H, s), 7.83 (1H, d, J = 9.1 Hz), 8.32 (1H, d, J = 5.1 Hz), 8.99 (2H, brs) | −117.1 | 0.06 | 1 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 51 | 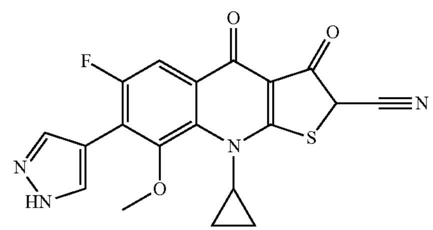 | 9-cyclopropyl-6-fluoro-8-methoxy-3,4-dioxo-7-(1H-pyrazol-4-yl)-2,3,4,9-tetrahydrothieno[2,3-b]quinoline-2-carbonitrile | HCl | 396.4 | 432.9 | 397 (M+H) | 0.99-1.01 (2H, m), 1.28-1.30 (2H, m), 3.58 (3H, s), 3.88-3.96 (1H, m), 7.78 (1H, d, J = 10.7 Hz), 8.19 (2H, d, J = 2.0 Hz) | −114.8 | 0.03 | 0.5 |
| 52 | 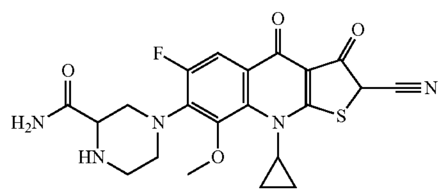 | 4-(2-cyano-9-cyclopropyl-6-fluoro-8-methoxy-3,4-dioxo-2,3,4,9-tetrahydrothieno[2,3-b]quinolin-7-yl)piperazine-2-carboxamide | HCl | 457.5 | 530.4 | 458 (M+H) | 0.99 (m, 2H), 1.23 (m, 2H), 3.15-3.61 (m, 5H), 3.73 (s, 3H), 3.85 (m, 2H), 4.06 (m, 1H), 7.68 (d, $J_{HF}$ = 12.0 Hz, 1H), 7.73 (s, 1H), 8.10 (s, 1H) | −123.8 | 0.25 | 2 |
| 53 | 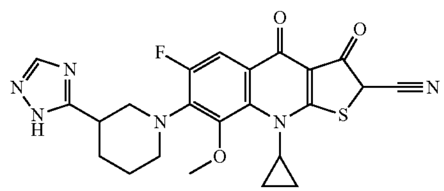 | 7-(3-(1H-1,2,4-triazol-5-yl)piperidin-1-yl)-9-cyclopropyl-6-fluoro-8-methoxy-3,4-dioxo-2,3,4,9-tetrahydrothieno[2,3-b]quinoline-2-carbonitrile | HCl | 480.5 | 517.0 | 481 (M+H) | 0.94 (m, 2H), 1.20 (m, 2H), 1.84 (m, 3H), 2.19 (m, 1H), 3.23 (m, 2H), 3.44 (m, 2H), 3.65 (s, 3H), 3.72 (m, 1H), 3.83 (m, 1H), 7.63 (d, $J_{HF}$ = 12.0 Hz, 1H), 8.75 (s, 1H) | −123.6 | 0.13 | 2 |
| 54 | 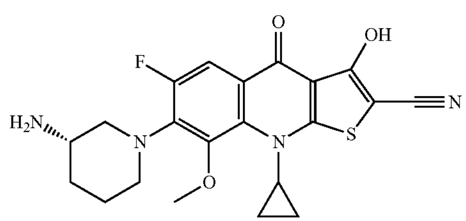 | (S)-7-(3-aminopiperidin-1-yl)-9-cyclopropyl-6-fluoro-3-hydroxyl-8-methoxy-4-oxo-4,9-dihydrothieno[2,3-b]quinoline-2-carbonitrile | HCl | 428.5 | 501.4 | 429 (M+H) | 0.95 (m, 2H), 1.23 (m, 2H), 1.50-2.12 (m, 4H), 3.03-3.41 (s, 3H), 3.40 (m, 4H), 3.66 (m, 2H), 7.66 (d, $J_{HF}$ = 12.0 Hz, 1H) | −123.7 | 0.13 | 0.5 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 55 | 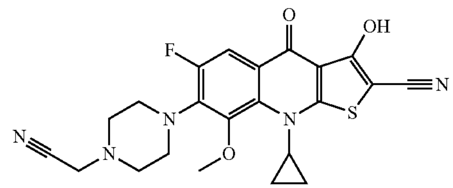 | 7-(4-(cyanomethyl)piperazin-1-yl)-9-cyclopropyl-6-fluoro-3-hydroxyl-8-methoxy-4-oxo-4,9-dihydrothieno[2,3-b]quinoline-2-carbonitrile | No salt | 453.5 | 453.5 | 454 (M + H) | 0.93-0.98 (2H, m), 1.15-1.26 (2H, m), 2.66 (4H, m), 3.39 (4H, m), 3.69 (3H, s), 3.84 (2H, s), 3.84-3.88 (1H, m), 7.64 (1H, d, J = 12.2 Hz), 11.17 (1H, brs) | −123.8 | 0.06 | 0.5 |
| 56 | 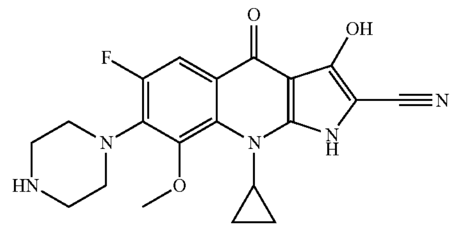 | 9-cyclopropyl-6-fluoro-3-hydroxyl-8-methoxy-4-oxo-7-(piperazin-1-yl)-4,9-dihydro-1H-pyrrolo[2,3-b]quinoline-2-carbonitrile | HCl | 397.4 | 470.3 | 398 (M + H) | TFA-d: 0.89-0.95 (m, 2H), 1.40-1.49 (m, 2H), 3.64-3.69 (m, 4H), 3.76 (s, 3H), 3.87-3.91 (m, 4H), 3.97-4.06 (m, 1H), 8.03 (d, J = 12.1 Hz) | −121.8 | ND | ND |
| 57 | 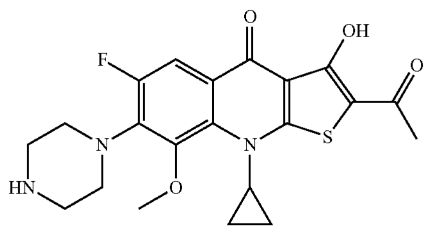 | 2-acetyl-9-cyclopropyl-6-fluoro-3-hydroxyl-8-methoxy-7-(piperazin-1-yl)thieno[2,3-b]quinolin-4(9H)-one | HCl | 431.5 | 467.9 | 432 (M + H) | 0.91-0.96 (2H, m), 1.20-1.24 (2H, m), 2.49 (3H, s), 3.26 (4H, m), 3.55 (4H, m), 3.73 (3H, s), 3.87-3.89 (1H, m), 7.69 (1H, d, J = 11.9 Hz), 9.13 (2H, brs) | −123.8 | 0.25 | 1 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 58 | 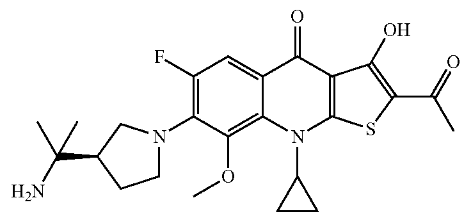 | (R)-2-acetyl-7-(3-(2-aminopropan-2-yl)pyrrolidin-1-yl)-9-cyclopropyl-6-fluoro-3-hydroxyl-8-methoxythieno[2,3-b]quinolin-4(9H)-one | HCl | 473.6 | 510.0 | 474 (M+H) | 0.96 (2H, m), 1.16-1.27 (2H, m), 1.33 (3H, s), 1.34 (3H, s), 1.79-1.85 (1H, m), 2.01-2.07 (1H, m), 2.48 (3H, s), 2.54-2.57 (1H, m), 3.52 (3H, s), 3.54-3.86 (5H, m), 7.57 (1H, d, J = 13.7 Hz), 8.29 (3H, brs) | −124.0 | 0.13 | 0.25 |
| 59 | 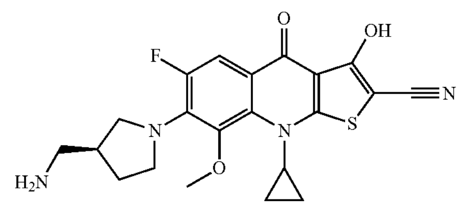 | (S)-7-(3-(aminomethyl)pyrrolidin-1-yl)-9-cyclopropyl-6-fluoro-3-hydroxyl-8-methoxy-4-oxo-dihydrothieno[2,3-b]quinoline-2-carbonitrile | HCl | 428.5 | 464.9 | 429 (M+H) | 0.84-0.89 (2H, m), 1.13-1.56 (2H, m), 1.67-1.73 (1H, m), 2.04-2.10 (1H, m), 2.36-2.44 (1H, m), 2.88 (2H, m), 3.44 (2H, s), 3.41-3.76 (5H, m), 7.51 (1H, d, J = 13.9 Hz), 7.96 (3H, brs) | −124.6 | 0.02 | <0.03 |
| 60 | 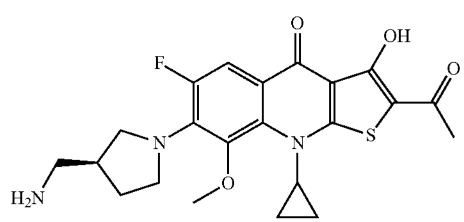 | (S)-2-acetyl-7-(3-(aminomethyl)pyrrolidin-1-yl)-9-cyclopropyl-6-fluoro-3-hydroxyl-8-methoxythieno[2,3-b]quinolin-4(9H)-one | HCl | 445.5 | 482.0 | 446 (M+H) | 0.91-0.96 (2H, m), 1.17-1.25 (2H, m), 1.74-1.80 (1H, m), 2.12-2.27 (1H, m), 2.51-2.56 (1H, m), 2.94-2.98 (2H, m), 2.47 (3H, s), 2.50-2.56 (1H, m), 3.51 (3H, s), 3.64-3.84 (5H, m), 7.57 (1H, d, J = 13.8 Hz), 8.02 (3H, brs) | −124.4 | 0.06 | 0.06 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 61 | 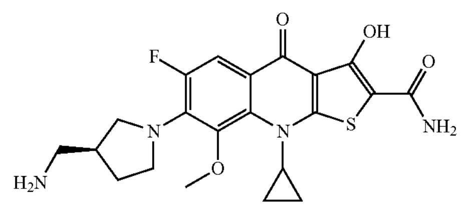 | (S)-7-(3-(aminomethyl)pyrrolidin-1-yl)-9-cyclopropyl-6-fluoro-3-hydroxyl-8-methoxy-4-oxo-4,9-dihydrothieno[2,3-b]quinoline-2-carboxamide | HCl | 446.5 | 483.0 | 447 (M+H) | 0.84-0.88 (2H, m), 1.15-1.18 (2H, m), 1.65-1.77 (1H, m), 2.04-2.12 (1H, m), 2.45-2.53 (1H, m), 2.88-2.91 (2H, m), 3.45 (3H, s), 3.41-3.76 (5H, m), 7.49 (1H, d, J = 13.9 Hz), 7.98 (3H, brs) | -125.0 | 0.13 | 0.5 |
| 62 | 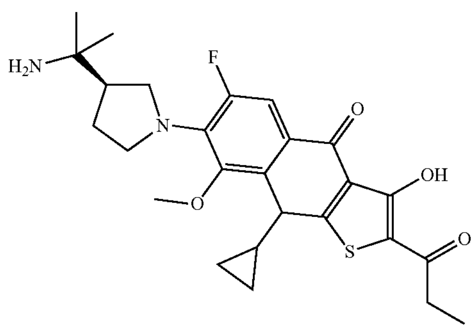 | (R)-7-(3-(2-aminopropan-2-yl)pyrrolidin-1-yl)-9-cyclopropyl-6-fluoro-3-hydroxy-8-methoxy-2-propionylthieno[2,3-b]quinolin-4(9H)-one | HCl | 487.6 | 524.0 | 488 (M+H) | 0.93-0.98 (2H, m), 1.08 (3H, t, J = 7.3 Hz), 1.14-1.27 (2H, m), 1.32 (3H, s), 1.33 (3H, s), 1.78-1.84 (1H, m), 2.04-2.07 (1H, m), 2.51-2.57 (1H, m), 2.84 (2H, q, J = 7.3 Hz), 3.51 (3H, s), 3.51-3.85 (5H, m), 7.49 (1H, d, J = 13.7 Hz), 8.32 (3H, brs) | -124.1 | 0.5 | 1 |

TABLE I-continued

| Cmp # | Structure | Name | Salt | MW | FW | MS | ¹H NMR | ¹⁹F NMR | MSSA | MRSA |
|---|---|---|---|---|---|---|---|---|---|---|
| 63 | 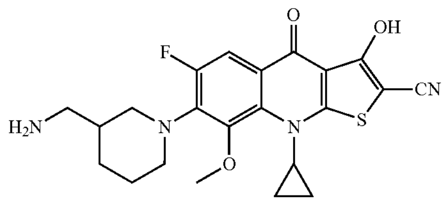 | 7-(3-(aminomethyl)piperidin-1-yl)-9-cyclopropyl-6-fluoro-3-hydroxyl-8-methoxy-4-oxo-dihydrothieno[2,3-b]quinoline-2-carbonitrile | HCl | 442.5 | 479.0 | 443 (M + H) | 0.93 (2H, m), 1.16-1.32 (3H, m), 1.61-1.99 (4H, m), 2.73-2.79 (2H, m), 2.95 (1H, t, J = 9.9 Hz), 3.13 (1H, t, J = 9.9 Hz), 3.36-3.53 (4H, m), 3.67 (3H, s), 3.79-3.87 (1H, m), 7.63 (1H, d, J = 11.97 Hz), 7.95 (3H, brs), 11.16 (1H, brs) | −123.5 | 0.03 | 0.13 |
| 64 | 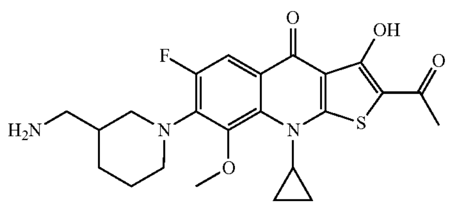 | 2-acetyl-7-(3-(aminomethyl)piperidin-1-yl)-9-cyclopropyl-6-fluoro-3-hydroxyl-8-methoxythieno[2,3-b]quinolin-4(9H)-one | HCl | 459.5 | 496.0 | 460 (M + H) | 0.91 (2H, m), 1.22-1.29 (3H, m), 1.61-1.99 (4H, m), 2.48 (3H, s), 2.72-2.78 (2H, m), 2.95 (1H, t, J = 9.9 Hz), 3.14 (1H, t, J = 9.9 Hz), 3.39 (1H, d, J = 12.0 Hz), 3.51 (1H, d, J = 12.0 Hz), 3.67 (3H, s), 3.83-3.88 (1H, m), 7.64 (1H, d, J = 11.9 Hz), 7.90 (3H, brs), 11.55 (1H, brs) | −123.2 | 0.13 | 0.25 |

TABLE I-continued

| Cmp # | Structure / Name | Salt | MW | FW | MS | ¹H NMR | ¹⁹F NMR | MSSA | MRSA |
|---|---|---|---|---|---|---|---|---|---|
| 65 | 7-(3-(aminomethyl)piperidin-1-yl)-9-cyclopropyl-6-fluoro-3-hydroxyl-8-methoxy-4-oxo-4,9-dihydrothieno[2,3-b]quinoline-2-carboxamide | HCl | 460.5 | 497.0 | 461 (M+H) | 0.91 (2H, m), 1.21-1.27 (3H, m), 1.62-2.02 (4H, m), 2.73-2.85 (2H, m), 2.96 (1H, t, J = 10.2 Hz), 3.14 (1H, t, J = 10.2 Hz), 3.38 (1H, d, J = 12.2 Hz), 3.52 (1H, t, J = 12.2 Hz), 3.68 (3H, s), 3.79-3.86 (1 H, m), 7.64 (1 H, d, J = 12.0 Hz), 8.04 (3H, brs) | −123.9 | 0.5 | 2 |
| 66 | 2-acetyl-7-(3-(2-amino-1-fluoroethylidene)piperidin-1-yl)-9-cycloprop-6-fluoro-3-hydroxyl-8-methoxythieno[2,3-b]quinolin-4(9H)-one | TFA | 489.5 | 603.6 | 490 (M+H) | D₂O: 0.91 (2H, m), 1.26 (2H, m), 1.73 (2H, m), 2.27 (3H, s), 2.49 (1H, m), 2.65 (1H, s), 3.38-4.02 (7H, m), 3.72 (3H, s), 6.85 (1H, d, J = 11.5 Hz) | D₂O: −123.1 (1F), −120.9 (1F) | 0.25 | 0.5 |

Note:
MSSA = *S. aureus* ATCC 29213; MRSA = fluoroquinolone-resistant *S. aureus* ATCC 700699; MIC in μg/mL Certain compounds discussed herein, in which $R_2$ is acetyl exhibit greatly reduced cellular toxicity and increased therapeutic index. Table II provides a comparison between several compounds for which the only difference whether the $R_2$ substituent is acetyl or cyano.
| Structure | MRSA (µg/ml) | Cytoxicity (Hep2, µM) |
|---|---|---|
| 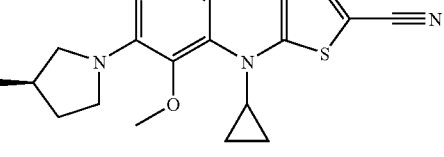 | 0.03 | 0.06 |
| 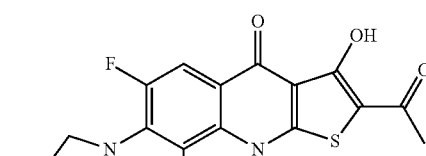 | 0.06 | 11 |
| 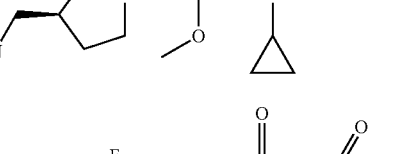 | 0.09 | 2 |
| 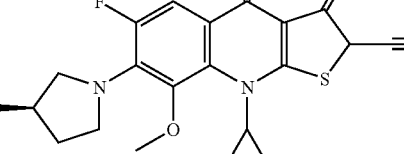 | 0.25 | 20 |
| 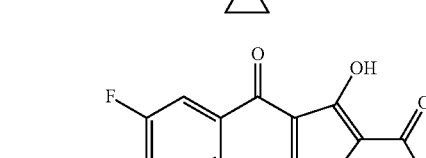 | 0.75 | 9 |
| 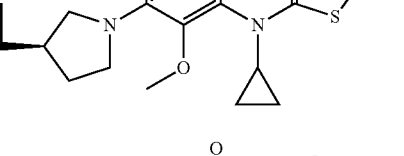 | 1 | 57 |

-continued

| Structure | MRSA (µg/ml) | Cytotoxicity (Hep2, µM) |
|---|---|---|
| [structure] | 0.13 | 0.4 |
| [structure] | 0.25 | 19 |

Example 13

Antimicrobial Activity of Compounds—Minimum Inhibitory Concentration (MIC) Assay The antimicrobial activity of the compounds of the invention may be evaluated by a number of methods, including the following visual minimum inhibitory concentration (MIC) assay. This assay determines the minimum concentration of compound required to inhibit growth of a bacterial strain.

Whole-cell antibacterial activity is determined by broth microdilution using conditions recommended by the NCCLS (see National Committee for Clinical Laboratory Standards. 2001. Performance standards for antimicrobial susceptibility testing: 11$^{th}$ informational supplement. Vol. 21, no. 1, M100-S11. National Committee for Clinical Laboratory Standards, Wayne, Pa.). Test compounds are dissolved in DMSO and diluted 1:50 in Mueller-Hinton II broth (Becton-Dickinson) to produce a 256 µg/ml stock solution. In a 96-well microtiter plate, the compound solution is serially two-fold diluted in Mueller-Hinton II broth. After the compounds are diluted, a 50 µl aliquot of the test organism (~1×10$^6$ cfu/mL) is added to each well of the microtiter plate. The final test concentrations ranges from 0.125-128 µg/mL. Inoculated plates are incubated in ambient air at 37° C. for 18 to 24 hours. The organisms selected for testing included laboratory strains S. aureus ATCC 29213 and E. coli ATCC 25922 (strains purchased from American Type Culture Collection, Manassas, Va.) m, S. aureus FQR700699, and Paeruginosa 27853. The minimum inhibitory concentration (MIC) is determined as the lowest concentration of compound that inhibited visible growth of the test organism.

Example 14

Cell Viability Staining with Alamar Blue

To determine whether the microcidal effect observed against S. aureus and E. coli is specific to bacterial cells, compounds are screened for cell viability effects on several human cell types.

Optimal cell density is first determined by plating cells in a 96-well plate standard sterile tissue culture plates in 100 µl media, 10% FBS at six cell densities from 500 cells/well to 15,000 cells/well. A cell free well containing only media is used as a control. Cells are incubated at 37° C. in a 5% $CO_2$ incubator for 24 hours. 10% culture volume (10 ul) of Alamar Blue (Biosource, DAL1100, 100 mL) is then added. Cells are incubated at 37° C. in a 5% $CO_2$ incubator and read in a Victor V plate reader, 544 nm excitation, 590 nm emission, at 3, 4, and 24 hours after the addition of Alamar Blue. The cell number vs. change in fluorescence is plotted to determine linearity of signal vs. cell number. The optimal density varies between 500-15,000 cells/well depending on the specific cell type. The optimal density is selected based on the highest number of cells that is still in the linear response range.

Determination of Compound Cytotoxicity

Cells are plated at optimal cell density in a standard sterile tissue culture 96 well plate, and incubated at 37° C., O/N in a 5% $CO_2$ incubator. 12 to 48 hours post-plating media is removed. The cells are washed 1 or 2 times with 1×PBS and replaced with fresh media containing the test compound in 1% DMSO. 24 to 72 hours after addition of compound, the media is removed, and the cells washed 1 to 2 times with 1×PBS. Fresh media containing 1/10 volume of Alamar Blue is then added. Plates are incubated 4 hours at 37° C. in a 5% $CO_2$ incubator and read in a Victor V plate reader, 544 nm excitation, 590 nm emission.

Compounds are diluted to 20 micromolar in 1% DMSO and media and screened in duplicate to obtain single concentration cytotoxicity data. Eight concentration points from 0.78 micromolar to 100 micromolar, run in duplicate, are used to determine cyclotoxicity CC50 values. Cells with 1% DMSO and media are used as a negative control, compounds having a known CC50 against a particular cell type are used as positive controls.

The change in fluorescence vs. concentration of test compound is plotted to determine the cytotoxicity of the compound.

What is claimed is:

1. A compound of the formula

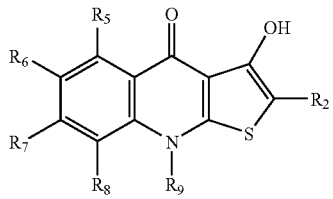

or a pharmaceutically acceptable salt thereof, wherein:

$R_2$ is cyano, amino, nitro, —$COR^b$, —$SO_2R^b$, trifluoromethyl, or phenyl substituted with 0 to 2 substituents independently chosen from halogen, $C_1$-$C_2$alkyl, or $C_1$-$C_2$alkoxy, where $R^b$ is hydroxyl, $C_1$-$C_6$alkoxy, $C_1$-$C_6$alkyl, aryl, aryloxy, —$N(R^a)_2$, or trifluoromethyl; and $R^a$ is independently chosen at each occurrence from hydrogen, $C_1$-$C_6$alkyl, and aryl;

$R_5$ is hydrogen, hydroxyl, halogen, $C_1$-$C_6$alkyl, or $C_1$-$C_6$alkoxy;

$R_6$ is hydrogen or halogen;

$R_7$ is phenyl or a C-linked 5- to 6-membered partially unsaturated heterocyclic group; or $R_7$ is a nitrogen-linked heterocycloalkyl group, which has 1 ring or 2 fused rings, a total of 4 to 8 ring members, including 0, 1, or 2 additional ring heteroatoms independently chosen from N, O, and S, or $R_7$ is a nitrogen-linked 6-membered heterocycloalkyl group, having 0, 1 or 2 additional ring heteroatoms independently chosen from N, O, and S, and bridged with a methylene or ethylene bridge;

Each of which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_2$-$C_6$alkenyl, $C_1$-$C_6$alkoxy, $C_1$-$C_2$haloalkyl, $C_1$-$C_2$haloalkoxy, and amino$C_1$-$C_2$alkyl, and (b) is oxo, amino, —$CONH_2$, $C_1$-$C_4$alkyl substituted with at least one hydroxyl or cyano, $C_1$-$C_6$alkylthio, $C_2$-$C_6$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, or $R_{10}$—O—N=, where $R_{10}$ is hydrogen or $C_1$-$C_6$alkyl, or $R_{13}R_{14}C=$ where $R_{13}$ is halogen and $R_{14}$ is amino$C_1$-$C_4$alkyl;

where each of (b) other than oxo, cyano, and —$CONH_2$, is substituted with 0 to 2 substituents independently chosen from halogen, hydroxyl, amino, cyano, nitro, oxo, —COOH, —$CONH_2$, $C_1$-$C_4$alkyl, $C_2$-$C_4$alkenyl, $C_2$-$C_4$alkynyl, $C_1$-$C_4$alkoxy, mono- and di-($C_1$-$C_4$alkyl)amino, $C_1$-$C_2$haloalkyl, and $C_1$-$C_2$haloalkoxy;

$R_8$ is methoxy or difluoromethoxy; and $R_9$ is $C_1$-$C_4$alkyl, $C_3$-$C_7$cycloalkyl, phenyl, or pyridyl, each of which $R_9$ is substituted with 0 to 3 substituents independently chosen from amino, halogen, $C_1$-$C_4$alkyl, and $C_1$-$C_4$alkoxy; or $R_8$ and $R_9$ are joined to form a 6-membered ring optionally containing one additional heteroatom chosen from N, O, and S, and optionally containing one carbon-carbon double bond.

2. A compound or salt of claim 1 wherein $R_7$ is

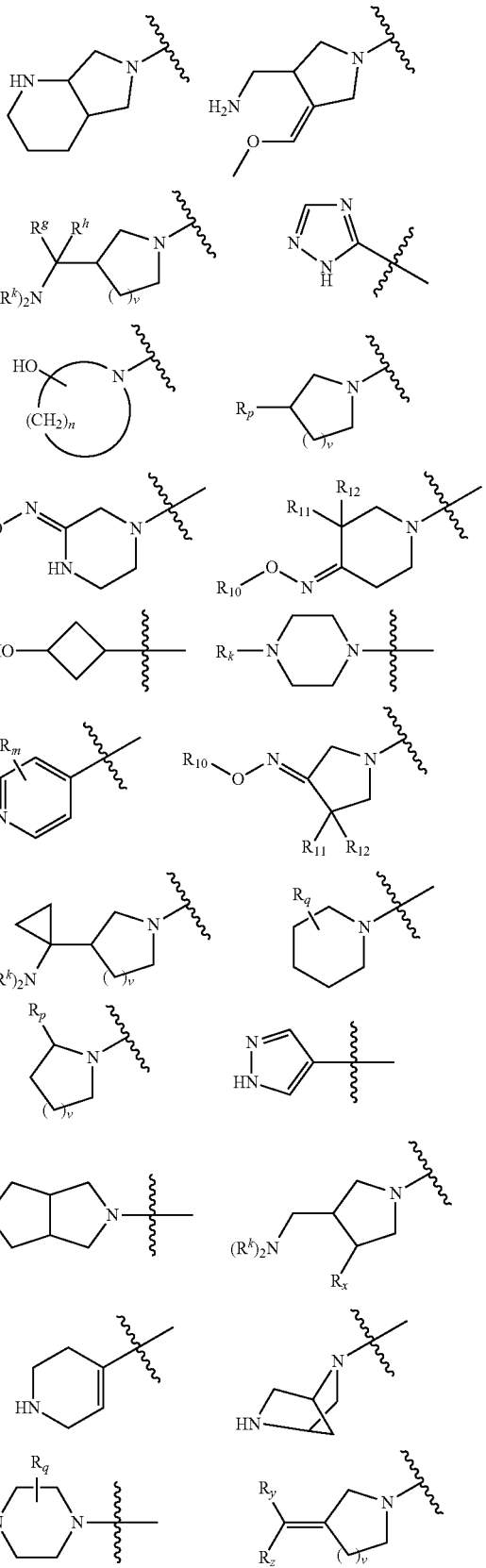

-continued

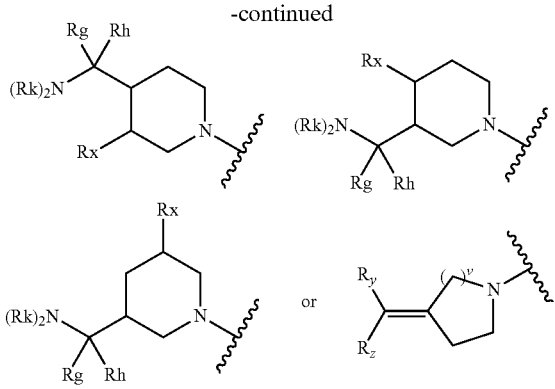

$R^g$ is hydrogen or $C_1$-$C_4$alkyl and $R^h$ is hydrogen or $C_1$-$C_6$alkyl;

$R^k$ is independently hydrogen, or $C_1$-$C_6$alkyl;

wherein $R^g$, and $R^h$, and $R^k$, when other than hydrogen, are substituted with 0 to 2 substituents independently chosen from halogen, hydroxyl, amino, cyano, and $C_1$-$C_2$alkoxy;

$R_m$ is $C_1$-$C_2$alkyl or piperazine;

$R_p$ is hydroxyl, amino, or $C_1$-$C_2$alkyl substituted with one hydroxyl, amino, or cyano substituent;

$R_q$ is amino, $(C_1$-$C_4$alkyl$)$amino$C_1$-$C_2$alkyl, amino$C_1$-$C_2$alkyl, —$CONH_2$, trifluoromethyl, or triazolyl;

$R_x$ is hydrogen or halogen;

One of $R_y$ and $R_z$ is halogen and the other is amino$C_1$-$C_4$alkyl;

n is an integer from 3 to 7;

v is 1, 2, or 3;

$R_{11}$ is amino or amino$C_1$-$C_4$alkyl and $R_{12}$ is hydrogen or amino$C_1$-$C_4$alkyl, or $R_{11}$ and $R_{12}$ are joined to form a 3 to 5 membered cycloalkyl group or a 3 to 5 membered heterocycloalkyl group having a single nitrogen atom.

3. A compound of or salt of claim 1 of the formula

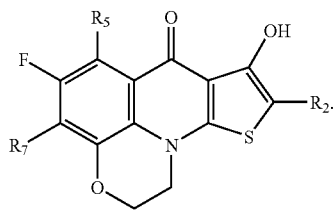

4. A compound of claim 1, wherein $R_5$ is hydrogen and $R_6$ is fluoro.

5. A compound or salt of claim 4, wherein $R_2$ is cyano, —$CONH_2$, or —$COR^b$, where $R^b$ is $C_1$-$C_2$alkyl or $C_1$-$C_2$alkoxy; and $R_5$ is hydrogen.

6. A compound or salt of claim 4, wherein $R_2$ is cyano, —$CONH_2$, or acetyl.

7. A compound or salt of claim 6, wherein $R_2$ is acetyl.

8. A compound or salt of claim 4, wherein $R_8$ is methoxy and $R_9$ is cyclopropyl.

9. A compound or salt of claim 4, wherein $R_7$ is a nitrogen-linked heterocycloalkyl group, which has 1 ring or two fused rings, a total of 4 to 8 ring members, including 0, 1, or 2 additional ring heteroatoms independently chosen from N, O, and S, which $R_7$ is substituted with 0 or 1 or more substituents independently chosen from (a) and 0 or 1 substituents chosen from (b); wherein (a) is chosen from halogen, hydroxyl, amino, nitro, $C_1$-$C_6$alkyl, $C_1$-$C_6$alkoxy, and amino($C_1$-$C_2$alkyl);

(b) is chosen from oxo, cyano, $C_1$-$C_4$alkyl substituted with at least one hydroxyl or cyano, $C_1$-$C_6$alkylthio, $C_2$-$C_4$alkanoyl, (mono- or di-$C_1$-$C_4$alkyl)amino$C_0$-$C_4$alkyl, ($C_3$-$C_7$cycloalkyl)$C_0$-$C_4$alkyl, ($C_3$-$C_7$cycloalkyl)amino$C_0$-$C_4$alkyl, ($C_3$-$C_7$cycloalkyl)($C_1$-$C_4$alkyl)amino$C_0$-$C_4$alkyl, (heterocycloalkyl)$C_0$-$C_4$alkyl, (5-membered heteroaryl)$C_0$-$C_4$alkyl, (aryl)$C_0$-$C_4$alkyl, $R_{10}$—O—N═, where $R_{10}$ is hydrogen or $C_1$-$C_6$alkyl, and $R_{13}R_{14}$C═, where $R_{13}$ is fluoro and $R_{14}$ is amino$C_1$-$C_2$alkyl;

where each of (b) other than oxo, —$CONH_2$, and cyano is substituted with 0 to 2 substituents independently chosen from halogen, hydroxyl, amino, cyano, nitro, oxo, —COOH, —$CONH_2$, $C_1$-$C_4$alkyl, $C_2$-$C_4$alkenyl, $C_1$-$C_4$alkoxy, mono- and di-($C_1$-$C_4$alkyl)amino, $C_1$-$C_2$haloalkyl, and $C_1$-$C_2$haloalkoxy.

10. A compound or salt of claim 9 wherein $R_7$ is a nitrogen-linked heterocycloalkyl group, which has one ring of 4 to 6 ring members and in which the only additional heteroatoms are 0 or 1 Nitrogen atoms;

which $R_7$ is substituted with 0, 1, or 2 substituents independently chosen from (a) and 0 or 1 substituents chosen from (b); wherein:

(a) is chosen from hydroxyl, amino, $C_1$-$C_2$alkyl, $C_1$-$C_2$alkoxy, trifluoromethyl, and amino($C_1$-$C_2$alkyl), and (b) is chosen from —$CONH_2$ $C_1$-$C_4$alkyl substituted with at least one cyano, triazolyl, (mono- and di-$C_1$-$C_4$alkyl)amino$C_0$-$C_4$alkyl, $R_{10}$—O═N—, where $R_{10}$ is hydrogen or $C_1$-$C_2$alkyl, and $R_{13}R_{14}$C═ where $R_{13}$ is fluoro and $R_{14}$ is aminomethyl, where each (b) other than —$CONH_2$ is substituted with 0 to 2 substituents independently chosen from halogen and cyano.

11. A compound or salt of claim 4, wherein $R_7$ is phenyl, triazolyl, pyridyl, or tetrahydropyridyl; or $R_7$ is a nitrogen-linked 6-membered heterocycloalkyl group, 0, 1 or 2 additional ring heteroatoms independently chosen from N, O, and S, and bridged with a methylene or ethylene bridge;

Each of which $R_7$ is substituted with 0 or 1 or more substituents independently chosen from (a) and 0 or 1 substituents chosen from (b); wherein (a) is chosen from halogen, hydroxyl, amino, $C_1$-$C_2$alkyl, $C_1$-$C_2$alkoxy, trifluoromethyl, trifluoromethoxy, and amino$C_1$-$C_2$alkyl, and (b) is chosen from oxo, $C_1$-$C_4$alkyl substituted with at least one hydroxyl or cyano, (mono- or di-$C_1$-$C_4$alkyl)amino$C_0$-$C_4$alkyl, and piperidinyl.

12. A compound or salt of claim 4 of the formula:

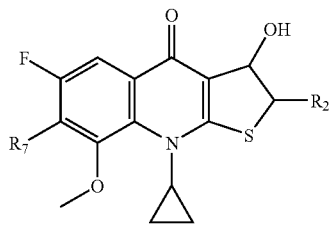

wherein $R_2$ is —CONH$_2$, acetyl, or cyano.

13. A compound or salt of claim 12, wherein $R_2$ is acetyl.

14. A compound or salt of claim 13, wherein $R^7$ is

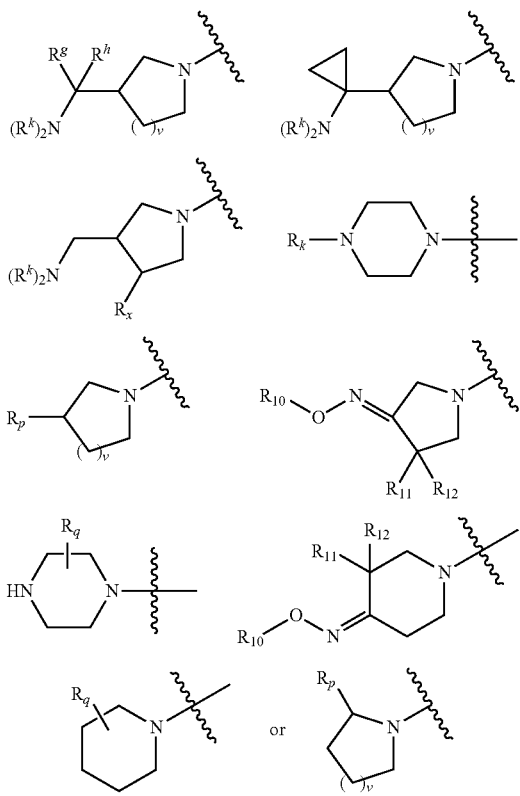

v is 1, 2, or 3;

$R^g$ is hydrogen or $C_1$-$C_4$alkyl and $R^h$ is hydrogen or $C_1$-$C_6$alkyl;

$R^k$ is independently hydrogen, or $C_1$-$C_6$alkyl;

wherein $R^g$, and $R^h$ and $R^k$, when other than hydrogen, are substituted with 0 to 2 substituents independently chosen from halogen, hydroxyl, amino, cyano, and $C_1$-$C_2$alkoxy;

$R_p$ is hydroxyl, amino, or $C_1$-$C_2$alkyl substituted with one hydroxyl, amino, or cyano substituent;

$R_q$ is amino, —CONH$_2$, trifluoromethyl, or triazolyl; and $R_x$ is halogen.

15. A compound or salt of claim 13 wherein $R_7$ is

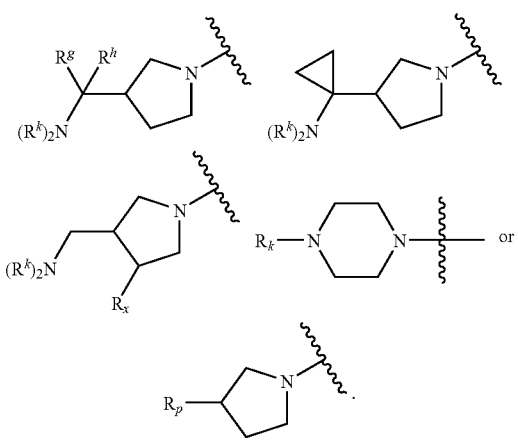

16. A compound or salt of claim 13, wherein $R_7$ is

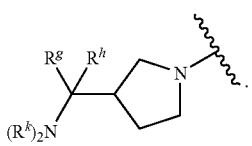

17. A compound or salt of claim 16, wherein $R^k$, $R^g$, and $R^h$ are all hydrogen.

18. A compound or salt of claim 13, wherein $R_7$ is

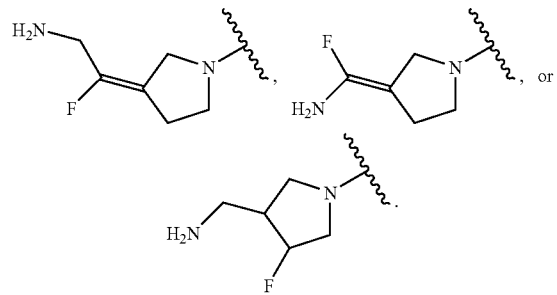

19. A compound or salt of claim 1, wherein the compound is (R)-methyl 7-(3-(2-aminopropan-2-yl)pyrrolidin-1-yl)-9-cyclopropyl-6-fluoro-3-hydroxyl-8-methoxy-4-oxo-4,9-dihydrothieno[2,3-b]quinoline-2-carboxylate;

(R)-7-(3-(2-aminopropan-2-yl)pyrrolidin-1-yl)-9-cyclopropyl-6-fluoro-3-hydroxyl-8-methoxythieno[2,3-b]quinolin-4(9H)-one;

methyl 9-cyclopropyl-6-fluoro-3-hydroxyl-8-methoxy-4-oxo-7-(piperazin-1-yl)-4,9-dihydrothieno[2,3-b]quinoline-2-carboxylate;

9-cyclopropyl-6-fluoro-3-hydroxyl-8-methoxy-7-(piperazin-1-yl)thieno[2,3-b]quinolin-4(9H)-one;

9-cyclopropyl-6-fluoro-3-hydroxyl-8-methoxy-4-oxo-7-(piperazin-1-yl)-4,9-dihydrothieno[2,3-b]quinoline-2-carbonitrile;

(R)-7-(3-(2-aminopropan-2-yl)pyrrolidin-1-yl)-9-cyclopropyl-6-fluoro-3-hydroxyl-8-methoxy-4-oxo-4,9-dihydrothieno[2,3-b]quinoline-2-carbonitrile;

7-((R)-3-((S)-1-aminoethyl)pyrrolidin-1-yl)-9-cyclopropyl-6-fluoro-3-hydroxyl-8-methoxy-4-oxo-4,9-dihydrothieno[2,3-b]quinoline-2-carbonitrile;

9-cyclopropyl-6-fluoro-3-hydroxyl-8-methoxy-7-(piperazin-1-yl)-2-pivaloylthieno[2,3-b]quinolin-4(9H)-one;

(R)-7-(3-(2-aminopropan-2-yl)pyrrolidin-1-yl)-9-cyclopropyl-6-fluoro-3-hydroxyl-8-methoxy-2-nitrothieno[2,3-b]quinolin-4(9H)-one;

9-cyclopropyl-6-fluoro-3-hydroxyl-8-methoxy-2-(phenylsulfonyl)-7-(piperazin-1-yl)thieno[2,3-b]quinolin-4(9H)-one;

9-cyclopropyl-2-(3,4-difluorophenyl)-6-fluoro-3-hydroxyl-8-methoxy-7-(piperazin-1-yl)thieno[2,3-b]quinolin-4(9H)-one;

9-cyclopropyl-8-(difluoromethoxy)-3-hydroxyl-4-oxo-7-(piperazin-1-yl)-4,9-dihydrothieno[2,3-b]quinoline-2-carbonitrile;

9-cyclopropyl-8-(difluoromethoxy)-7-(dimethylamino)-3-hydroxyl-4-oxo-4,9-dihydrothieno[2,3-b]quinoline-2-carbonitrile;

9-cyclopropyl-8-(difluoromethoxy)-6-fluoro-3-hydroxyl-4-oxo-7-(piperazin-1-yl)-4,9-dihydrothieno[2,3-b]quinoline-2-carbonitrile;

7-(4-(cyanomethyl)piperazin-1-yl)-9-cyclopropyl-8-(difluoromethoxy)-6-fluoro-3-hydroxyl-4-oxo-4,9-dihydrothieno[2,3-b]quinoline-2-carbonitrile;

9-cyclopropyl-3-hydroxyl-8-methoxy-4-oxo-7-(piperazin-1-yl)-4,9-dihydrothieno[2,3-b]quinoline-2-carbonitrile;

9-cyclopropyl-6-fluoro-3-hydroxyl-8-methoxy-7-(piperazin-1-yl)-2-(2,2,2-trifluoroacetyl)thieno[2,3-b]quinolin-4(9H)-one;

(R)-7-(3-(2-aminopropan-2-yl)pyrrolidin-1-yl)-9-cyclopropyl-3-hydroxyl-8-methoxy-4-oxo-4,9-dihydrothieno[2,3-b]quinoline-2-carbonitrile;

9-cyclopropyl-6-fluoro-3-hydroxyl-4-oxo-7-(piperazin-1-yl)-4,9-dihydrothieno[2,3-b]quinoline-2-carbonitrile;

(S)-7-(3-aminopyrrolidin-1-yl)-9-cyclopropyl-6-fluoro-3-hydroxyl-8-methoxy-4-oxo-4,9-dihydrothieno[2,3-b]quinoline-2-carbonitrile;

(S)-9-cyclopropyl-6-fluoro-3-hydroxyl-7-(3-hydroxylpyrrolidin-1-yl)-8-methoxy-4-oxo-4,9-dihydrothieno[2,3-b]quinoline-2-carbonitrile;

9-cyclopropyl-6-fluoro-3-hydroxyl-7-(3-hydroxylazetidin-1-yl)-8-methoxy-4-oxo-4,9-dihydrothieno[2,3-b]quinoline-2-carbonitrile;

9-cyclopropyl-6-fluoro-3-hydroxyl-8-methoxy-4-oxo-7-(piperazin-1-yl)-4,9-dihydrothieno[2,3-b]quinoline-2-carboxamide;

9-cyclopropyl-6-fluoro-3-hydroxyl-8-methoxy-7-(4-methylpiperazin-1-yl)-4-oxo-4,9-dihydrothieno[2,3-b]quinoline-2-carbonitrile;

9-cyclopropyl-6-fluoro-3-hydroxyl-8-methoxy-7-(2-methylpyridin-4-yl)-4-oxo-4,9-dihydrothieno[2,3-b]quinoline-2-carbonitrile;

9-cyclopropyl-3-hydroxyl-8-methoxy-4-oxo-7-4aS,7aS)-tetrahydro-1H-pyrrolo[3,4-b]pyridin-6(2H,7H,7aH)-yl)-4,9-dihydrothieno[2,3-b]quinoline-2-carbonitrile;

(S)-7-(3-aminopyrrolidin-1-yl)-9-cyclopropyl-6-fluoro-3-hydroxyl-8-methoxy-4-oxo-4,9-dihydro-1H-pyrrolo[2,3-b]quinoline-2-carbonitrile;

7-(4-aminopiperidin-1-yl)-9-cyclopropyl-6-fluoro-3-hydroxyl-8-methoxy-4-oxo-4,9-dihydrothieno[2,3-b]quinoline-2-carbonitrile;

9-cyclopropyl-7-((R)-3-((S)-1-(ethylamino)ethyl)pyrrolidin-1-yl)-6-fluoro-3-hydroxyl-8-methoxy-4-oxo-4,9-dihydrothieno[2,3-b]quinoline-2-carbonitrile;

9-cyclopropyl-6-fluoro-3-hydroxyl-8-methoxy-7-((R)-3-((S)-1-(methylamino)ethyl)pyrrolidin-1-yl)-4-oxo-4,9-dihydrothieno[2,3-b]quinoline-2-carbonitrile;

(R)-7-(3-(2-aminopropan-2-yl)pyrrolidin-1-yl)-9-cyclopropyl-6-fluoro-3-hydroxyl-8-methoxy-4-oxo-4,9-dihydrothieno[2,3-b]quinoline-2-carboxamide;

9-cyclopropyl-7-((R)-3-((S)-1-(dimethylamino)ethyl)pyrrolidin-1-yl)-6-fluoro-3-hydroxyl-8-methoxy-4-oxo-4,9-dihydrothieno[2,3-b]quinoline-2-carbonitrile;

9-cyclopropyl-6-fluoro-7-((R)-3-(S)-1-(2-fluoroethylamino)ethyl)pyrrolidin-1-yl)-3-hydroxyl-8-methoxy-4-oxo-4,9-dihydrothieno[2,3-b]quinoline-2-carbonitrile;

(R)-9-cyclopropyl-6-fluoro-3-hydroxyl-8-methoxy-7-(3-(2-(methylamino)propan-2-yl)pyrrolidin-1-yl)-4-oxo-4,9-dihydrothieno[2,3-b]quinoline-2-carbonitrile;

(R)-9-cyclopropyl-7-(3-(2-(ethylamino)propan-2-yl)pyrrolidin-1-yl)-6-fluoro-3-hydroxyl-8-methoxy-4-oxo-4,9-dihydrothieno[2,3-b]quinoline-2-carbonitrile;

(R)-9-cyclopropyl-7-(3-(2-(dimethylamino)propan-2-yl)pyrrolidin-1-yl)-6-fluoro-3-hydroxyl-8-methoxy-4-oxo-4,9-dihydrothieno[2,3-b]quinoline-2-carbonitrile;

1-(2-cyano-9-cyclopropyl-6-fluoro-3-hydroxyl-8-methoxy-4-oxo-4,9-dihydrothieno[2,3-b]quinolin-7-yl)piperidine-3-carboxamide;

9-cyclopropyl-6-fluoro-3-hydroxyl-8-methoxy-4-oxo-7-((4aS,7aS)-tetrahydro-1H-pyrrolo[3,4-b]pyridin-6(2H,7H,7aH)-yl)-4,9-dihydrothieno[2,3-b]quinoline-2-carbonitrile;

(Z)-7-(3-(aminomethyl)-4-(methoxyimino)pyrrolidin-1-yl)-9-cyclopropyl-6-fluoro-3-hydroxyl-8-methoxy-4-oxo-4,9-dihydrothieno[2,3-b]quinoline-2-carbonitrile;

9-cyclopropyl-6-fluoro-3-hydroxyl-8-methoxy-4-oxo-7-(1,2,3,6-tetrahydropyridin-4-yl)-4,9-dihydrothieno[2,3-b]quinoline-2-carbonitrile;

7-(2,5-diazabicyclo[2.2.1]heptan-2-yl)-9-cyclopropyl-6-fluoro-3-hydroxyl-8-methoxy-4-oxo-4,9-dihydrothieno[2,3-b]quinoline-2-carbonitrile;

9-cyclopropyl-6-fluoro-7-((3aR,6aS)-hexahydropyrrolo[3,4-c]pyrrol-2(1H)-yl)-3-hydroxyl-8-methoxy-4-oxo-4,9-dihydrothieno[2,3-b]quinoline-2-carbonitrile;

9-cyclopropyl-6-fluoro-8-methoxy-3,4-dioxo-7-(4-(trifluoromethyl)piperidin-1-yl)-2,3,4,9-tetrahydrothieno[2,3-h]quinoline-2-carbonitrile;

7-((R)-3-(1H-1,2,4-triazol-5-yl)pyrrolidin-1-yl)-9-cyclopropyl-6-fluoro-8-methoxy-3,4-dioxo-2,3,4,9-tetrahydrothieno[2,3-h]quinoline-2-carbonitrile;

1-(2-cyano-9-cyclopropyl-6-fluoro-8-methoxy-3,4-dioxo-2,3,4,9-tetrahydrothieno[2,3-b]quinolin-7-yl)piperidine-4-carboxamide;

(2S)-1-(2-cyano-9-cyclopropyl-6-fluoro-8-methoxy-3,4-dioxo-2,3,4,9-tetrahydrothieno[2,3-b]quinolin-7-yl)pyrrolidine-2-carboxamide;

(1S)-5-fluoro-1-methyl-7,8-dioxo-4-(piperazin-1-yl)-2,7,8,9-tetrahydro-1H-[1,4]oxazino[2,3,4-ij]thieno[2,3-b]quinoline-9-carbonitrile;

7-(4-(1H-1,2,4-triazol-5-yl)piperidin-1-yl)-9-cyclopropyl-6-fluoro-8-methoxy-3,4-dioxo-2,3,4,9-tetrahydrothieno[2,3-h]quinoline-2-carbonitrile;

7-((R)-3-(2-(2-cyanoethylamino)propan-2-yl)pyrrolidin-1-yl)-9-cyclopropyl-6-fluoro-8-methoxy-3,4-dioxo-2,3,4,9-tetrahydrothieno[2,3-h]quinoline-2-carbonitrile;

9-cyclopropyl-6-fluoro-8-methoxy-3,4-dioxo-7-(2-(piperazin-1-yl)pyridin-4-yl)-2,3,4,9-tetrahydrothieno[2,3-h]quinoline-2-carbonitrile;

9-cyclopropyl-6-fluoro-8-methoxy-3,4-dioxo-7-(1H-pyrazol-4-yl)-2,3,4,9-tetrahydrothieno[2,3-b]quinoline-2-carbonitrile;

4-(2-cyano-9-cyclopropyl-6-fluoro-8-methoxy-3,4-dioxo-2,3,4,9-tetrahydrothieno[2,3-b]quinolin-7-yl)piperazine-2-carboxamide;

7-(3-(1H-1,2,4-triazol-5-yl)piperidin-1-yl)-9-cyclopropyl-6-fluoro-8-methoxy-3,4-dioxo-2,3,4,9-tetrahydrothieno[2,3-h]quinoline-2-carbonitrile;

(S)-7-(3-aminopiperidin-1-yl)-9-cyclopropyl-6-fluoro-3-hydroxyl-8-methoxy-4-oxo-4,9-dihydrothieno[2,3-h]quinoline-2-carbonitrile;

7-(4-(cyanomethyl)piperazin-1-yl)-9-cyclopropyl-6-fluoro-3-hydroxyl-8-methoxy-4-oxo-4,9-dihydrothieno[2,3-h]quinoline-2-carbonitrile;

9-cyclopropyl-6-fluoro-3-hydroxyl-8-methoxy-4-oxo-7-(piperazin-1-yl)-4,9-dihydro-1H-pyrrolo[2,3-b]quinoline-2-carbonitrile;

2-acetyl-9-cyclopropyl-6-fluoro-3-hydroxyl-8-methoxy-7-(piperazin-1-yl)thieno[2,3-h]quinolin-4(9H)-one;

(R)-2-acetyl-7-(3-(2-aminopropan-2-yl)pyrrolidin-1-yl)-9-cyclopropyl-6-fluoro-3-hydroxyl-8-methoxythieno[2,3-b]quinolin-4(9H)-one;

(S)-7-(3-(aminomethyl)pyrrolidin-1-yl)-9-cyclopropyl-6-fluoro-3-hydroxyl-8-methoxy-4-oxo-4,9-dihydrothieno[2,3-b]quinoline-2-carbonitrile;

(S)-2-acetyl-7-(3-(aminomethyl)pyrrolidin-1-yl)-9-cyclopropyl-6-fluoro-3-hydroxyl-8-methoxythieno[2,3-b]quinolin-4(9H)-one;

(S)-7-(3-(aminomethyl)pyrrolidin-1-yl)-9-cyclopropyl-6-fluoro-3-hydroxyl-8-methoxy-4-oxo-4,9-dihydrothieno[2,3-b]quinoline-2-carboxamide;

(R)-7-(3-(2-aminopropan-2-yl)pyrrolidin-1-yl)-9-cyclopropyl-6-fluoro-3-hydroxyl-8-methoxy-2-propionylthieno[2,3-b]quinolin-4(9H)-one;

7-(3-(aminomethyl)piperidin-1-yl)-9-cyclopropyl-6-fluoro-3-hydroxyl-8-methoxy-4-oxo-4,9-dihydrothieno[2,3-b]quinoline-2-carbonitrile;

2-acetyl-7-(3-(aminomethyl)piperidin-1-yl)-9-cyclopropyl-6-fluoro-3-hydroxyl-8-methoxythieno[2,3-b]quinolin-4(9H)-one;

7-(3-(aminomethyl)piperidin-1-yl)-9-cyclopropyl-6-fluoro-3-hydroxyl-8-methoxy-4-oxo-4,9-dihydrothieno[2,3-b]quinoline-2-carboxamide; or 2-acetyl-7-(3-(2-amino-1-fluoroethylidene)piperidin-1-yl)-9-cyclopropyl-6-fluoro-3-hydroxyl-8-methoxythieno[2,3-b]quinolin-4(9H)-one.

20. A pharmaceutical composition comprising a compound or salt of claim 1 together with a pharmaceutically acceptable carrier.

21. A method of treating a Methicillin Resistant Staphylococcus Aureus (MRSA) infection in a patient comprising administering a compound or salt of claim 1 to the patient.

* * * * *